(12) United States Patent
Mou et al.

(10) Patent No.: US 12,101,919 B2
(45) Date of Patent: Sep. 24, 2024

(54) WEARABLE DISPLAY DEVICE

(71) Applicants: Microjet Technology Co., Ltd., Hsinchu (TW); Hsiu Ying Tseng, New Taipei (TW)

(72) Inventors: Hao-Jan Mou, Hsinchu (TW); Ta-Wei Hsueh, Hsinchu (TW); Yu-Tzu Chen, Hsinchu (TW); Shou-Cheng Cheng, Hsinchu (TW); Chi-Feng Huang, Hsinchu (TW); Yung-Lung Han, Hsinchu (TW); Tsung-I Lin, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 763 days.

(21) Appl. No.: 17/357,286

(22) Filed: Jun. 24, 2021

(65) Prior Publication Data
US 2022/0007538 A1  Jan. 6, 2022

(30) Foreign Application Priority Data

Jul. 3, 2020 (TW) ................................ 109122668

(51) Int. Cl.
| | |
|---|---|
| H05K 7/20 | (2006.01) |
| A61B 3/16 | (2006.01) |
| A61B 5/00 | (2006.01) |
| G06F 1/16 | (2006.01) |
| G06F 1/20 | (2006.01) |
| H02N 2/02 | (2006.01) |
| H10N 30/20 | (2023.01) |

(52) U.S. Cl.
CPC ........... *H05K 7/2099* (2013.01); *A61B 3/165* (2013.01); *A61B 5/7445* (2013.01); *G06F 1/163* (2013.01); *G06F 1/203* (2013.01); *H02N 2/02* (2013.01); *H05K 7/20327* (2013.01); *H05K 7/20336* (2013.01); *H10N 30/20* (2023.02); *A61B 2562/0247* (2013.01); *G06F 2200/201* (2013.01)

(58) Field of Classification Search
None
See application file for complete search history.

(56) References Cited

U.S. PATENT DOCUMENTS

2019/0107870 A1   4/2019 Ali

FOREIGN PATENT DOCUMENTS

| CN | 107645921 A | 1/2018 |
|---|---|---|
| CN | 108345109 A | 7/2018 |
| CN | 207783399 U | 8/2018 |

(Continued)

*Primary Examiner* — Xanthia C Relford
(74) *Attorney, Agent, or Firm* — Birch, Stewart, Kolasch & Birch, LLP

(57) ABSTRACT

A wearable display device is disclosed and includes a main body, a heat dissipation processing module and an inflatable actuation module. The main body includes a front cover, a lateral cover, an inflatable airbag, a circuit board and a microprocessor. The heat dissipation processing module is configured to perform heat exchange with the microprocessor, and includes a first actuator, a heat pipe and a cooling chip. The inflatable actuation module includes a base, a ventilation channel, a second actuator and a valve component. When the second actuator and the valve component are driven, the valve component is opened and the second actuator is enabled, the gas is transported and inflates the inflatable airbag through the ventilation channel, so that the main body is stably fitted and positioned on the head of the wearer.

21 Claims, 34 Drawing Sheets

(56) References Cited

FOREIGN PATENT DOCUMENTS

| | | |
|---|---|---|
| CN | 108508605 A | 9/2018 |
| CN | 208013561 U | 10/2018 |
| CN | 209182579 U | 7/2019 |
| CN | 111007666 A | 4/2020 |
| CN | 111225615 A | 6/2020 |
| JP | 7-171113 A | 7/1995 |
| TW | 201742595 A | 12/2017 |
| TW | 201916786 A | 4/2019 |
| TW | 201935080 A | 9/2019 |
| TW | 202014979 A | 4/2020 |
| WO | WO 2017/061839 A1 | 4/2017 |

WEARABLE DISPLAY DEVICE

FIELD OF THE INVENTION

The present disclosure relates to a wearable display device, and more particularly to a head-mounted device having an ultra-thin fluid pump used for heat dissipation or inflation of an electronic device which can be combined with an eye pressure detection.

BACKGROUND OF THE INVENTION

With the rapid development of life science and technology in recent years, the specifications, equipment and functions of virtual reality-related peripheral devices have been rapidly upgraded. In order to satisfy the requirements thereof, the efficacy of processing chip inside the wearable display device must also be greatly improved. However, if the heat generated by the processing chip during operation under high-speed cannot be removed quickly, the performance thereof will be greatly affected. In addition, when the wearable device is used for a long time, it is necessary to consider the comfortability of the wearable device while wearing. Moreover, when the wearable device is used for a long time, it has to avoid excessive use of the eyes and causing dizziness or excessive intraocular pressure which are harmful to the health. In view of this shortcoming, how to provide a wearable display device that can improve the above-mentioned problems is actually an issue needs to resolve right now.

SUMMARY OF THE INVENTION

An object of the present disclosure is to provide a wearable display device. By using a first actuator with a micro pump structure to construct a heat dissipation processing module for heat dissipation of a micro-processing chip inside the wearable display device, the operating efficiency of the wearable display device is improved, which not only miniaturizes the entire device but also dissipates the heat silently. By using a second actuator with the micro pump structure to inflate an airbag, the wearable display device can be worn more comfortably during long-term use. Moreover, by using a third actuator with the micro pump structure combined with an intraocular pressure sensor, the intraocular pressure of the wearer can be detected and provide a warning to avoid excessive use of the eyes and causing dizziness or excessive intraocular pressure which are harmful to health.

In accordance with an aspect of the present disclosure, a wearable display device includes a main body, a heat dissipation processing module and an inflatable actuation module is provided. The main body includes a front cover, a lateral cover, an inflatable airbag, a circuit board and a microprocessor. The lateral cover is connected to one side of the front cover, the inflatable airbag is attached to and positioned at one side of the lateral cover, the circuit board is positioned inside the lateral cover, and the microprocessor is packaged on the circuit board. The heat dissipation processing module includes a first actuator, a heat pipe and at least one cooling chip. The heat pipe is contacted with a heat-generating surface of the microprocessor, the heat pipe is configured to receive a heat dissipation liquid, the first actuator and the at least one cooling chip are connected to the heat pipe and perform heat exchange on the heat pipe. The inflatable actuation module is disposed on the circuit board and includes a base, a ventilation channel, a second actuator and a valve component. The base is positioned at the circuit board and in fluid communication with the ventilation channel, the second actuator is positioned in the base, the ventilation channel is in fluid communication with the inflatable airbag, and the valve component covers the second actuator and is capable of being opened or closed. When the second actuator and the valve component are driven, the valve component is opened, and the second actuator is enabled at the same time, whereby gas is transported through the ventilation channel to inflate the inflatable airbag.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

Figure 1:
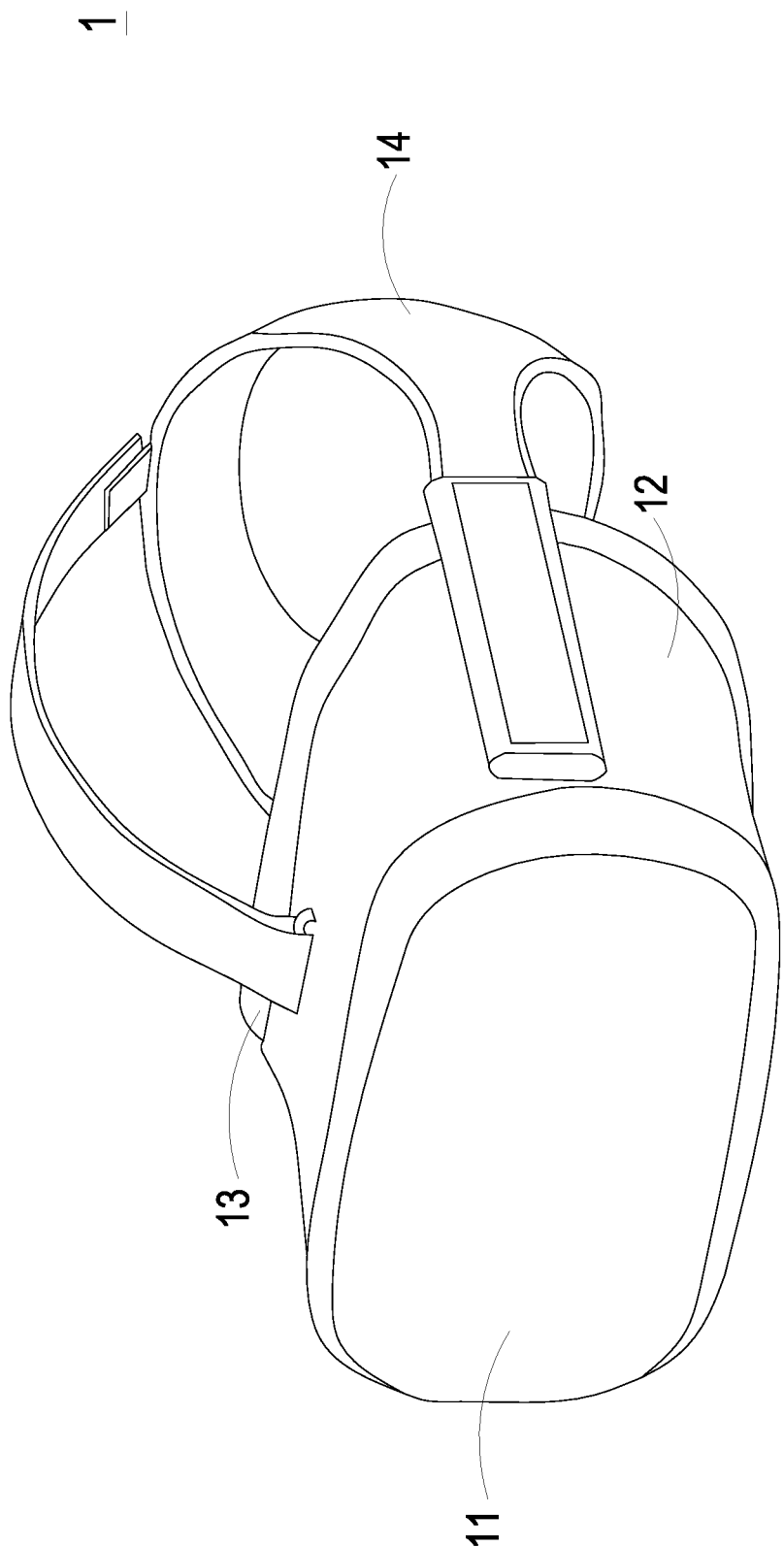
FIG. 1 is a schematic view illustrating a wearable display device according to an embodiment of the present disclosure.

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Please refer to FIG. 1 to FIG. 4. The present disclosure provides a wearable display including a main body 1, a heat dissipation processing module 2 and an inflatable actuation 3. In this embodiment, the main body 1 includes a front cover 11, a lateral cover 12, an inflatable airbag 13, a headband 14, a circuit board 15, a microprocessor 16, a communicator 17 and at least one display 18. The lateral cover 12 is connected to one side of the front cover 11. The inflatable airbag 13 is attached to and positioned at one side of the lateral cover 12. The at least one display 18 is disposed and positioned at the side of the front cover 11. The headband 14 is connected to the lateral cover 12. The lateral cover 12 is disposed between the front cover 11 and the inflatable airbag 13. The main body 1 allows to be worn through the headband 14. The inflatable airbag 13 can provide the positioning effect and comfortability while wearing. The circuit board 15 is positioned inside the lateral cover 12, and the microprocessor 16 and the communicator 17 are packaged on the circuit board 15. Moreover, the wireless two-way data transmission of the wearable display is provided by the communicator 17 through Bluetooth or Wi-Fi. The data can be received by the communicator 17 and provided to the microprocessor 16 to calculate and process, so that the at least one display 18 generates an image data and displays an image processed by the microprocessor 16. Notably, the at least one display 18 can be, for example, two separated displays 18 disposed inside the lateral cover 12, respectively, but not limited thereto. The at least one display 18 can also be a complete set of displays 18 disposed inside the lateral cover 12. It can be understood that the display 18 is also electrically connected to the circuit board 15 and the microprocessor 16, so as to display the image processed by the microprocessor 16.

Figure 2A:
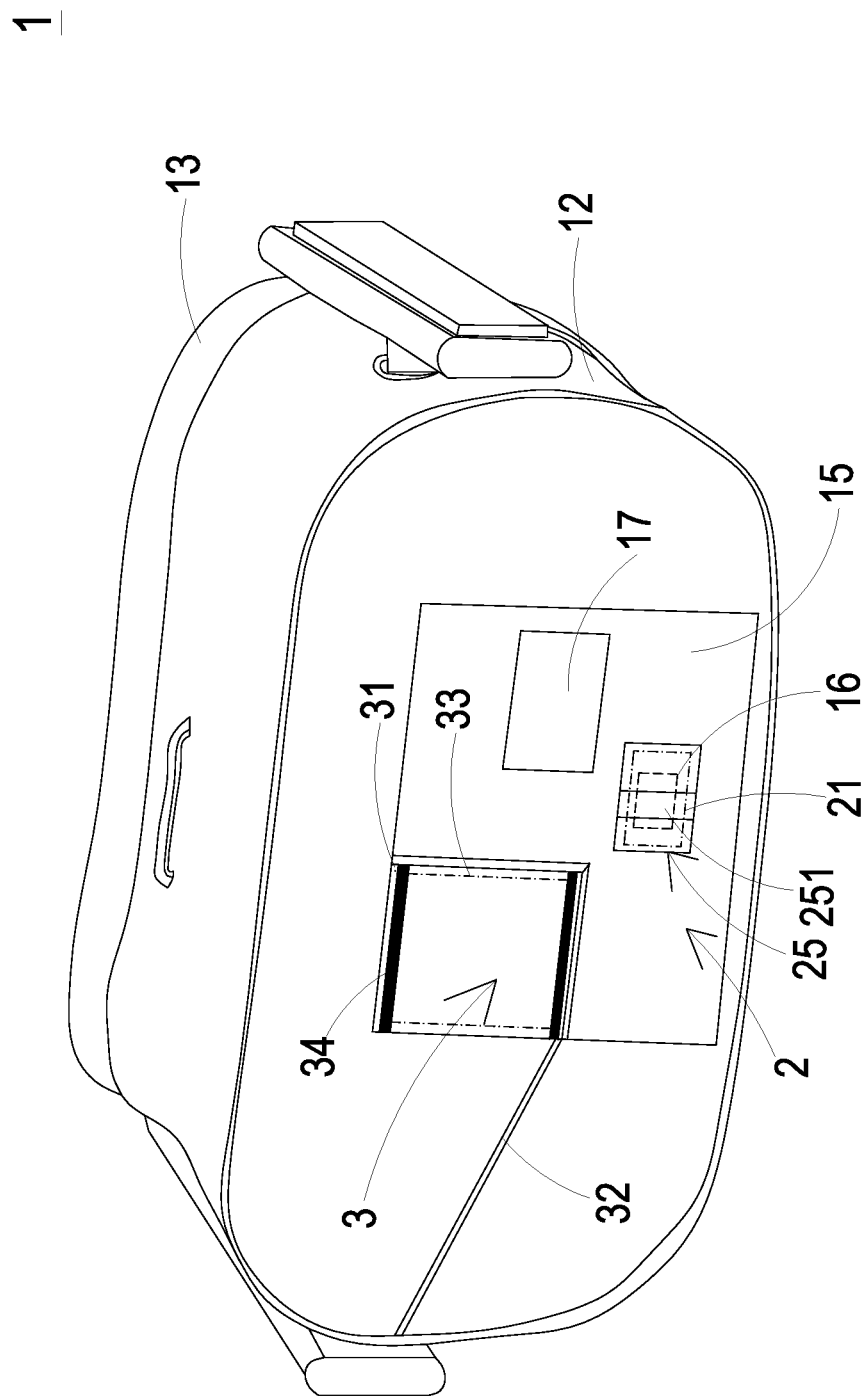
FIG. 2A is a schematic view illustrating a microprocessor on the circuit board of the wearable display device according to an embodiment of the present disclosure.
Figure 2B:
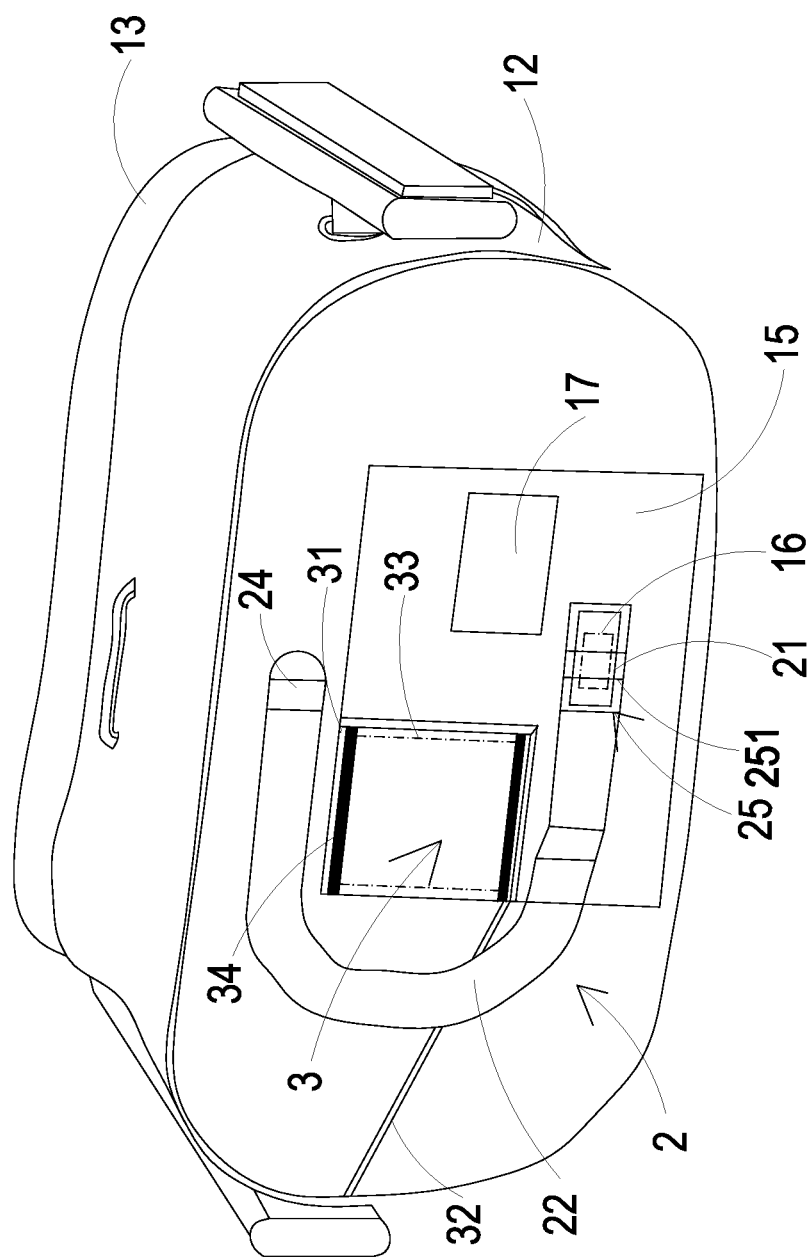
FIG. 2B is a schematic view illustrating a microprocessor on the circuit board of the wearable display device according to another embodiment of the present disclosure.
Figure 5A:
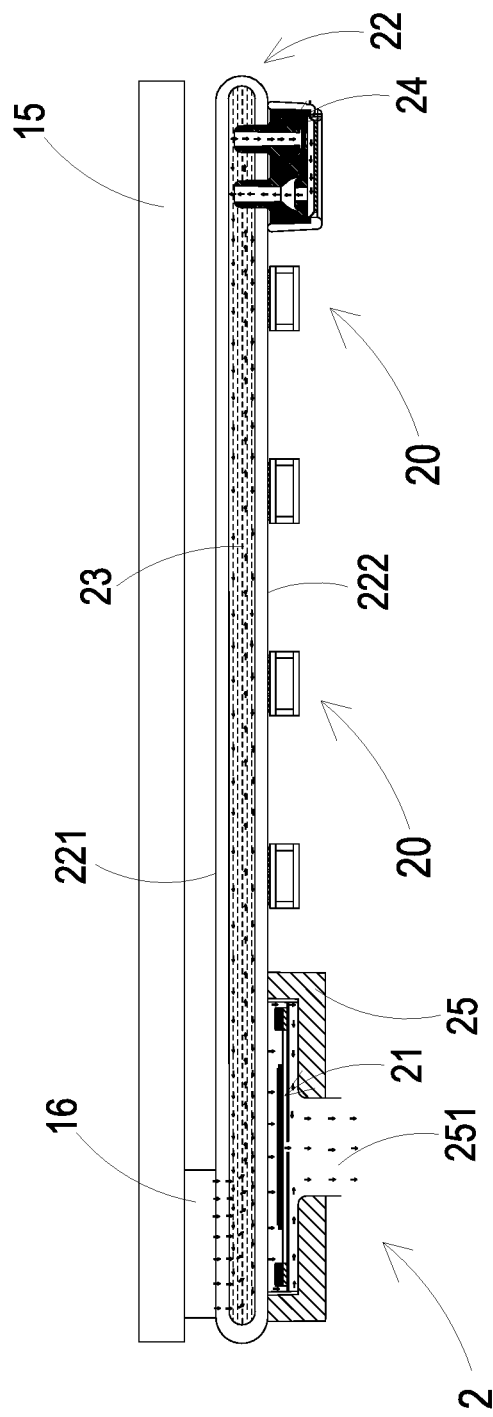
FIG. 5A is a cross sectional view illustrating a heat dissipation processing module of the wearable display device according to an embodiment of the present disclosure.
Figure 5B:
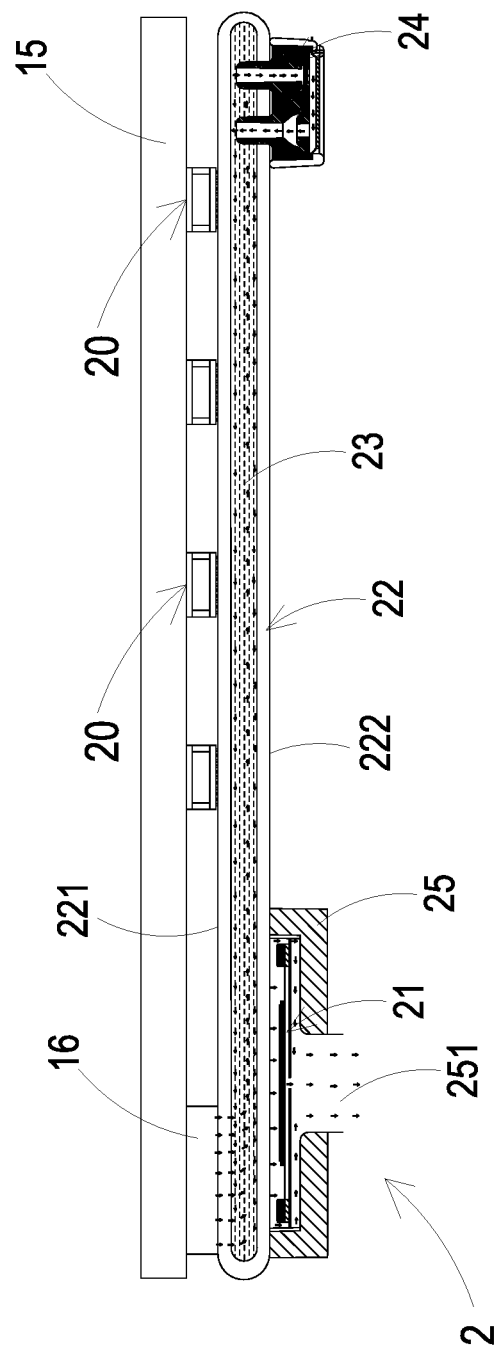
FIG. 5B is a cross sectional view illustrating a heat dissipation processing module of the wearable display device according to another embodiment of the present disclosure.

As shown in FIG. 2B and FIG. 5A, this embodiment exemplifies the heat dissipation processing module 2 of the microprocessor 16 on the circuit board 15 for heat dissipation. In the embodiment, the heat dissipation processing module 2 includes at least one cooling chip 20, a first actuator 21, a heat pipe 22 and a positioning accommodation seat 25. The heat pipe 22 is contacted with a heat-generating surface of the microprocessor 16, so that the heat generated from the microprocessor 16 can be dissipated directly through heat exchange. The heat pipe 22 is configured to receive a heat dissipation liquid 23, the first actuator 21 and the at least one cooling chip 20 are connected to the heat pipe 22 to perform thermal convection on the heat pipe 22, so as to accelerate the convective heat exchange from the heat source of the microprocessor 16 by the heat pipe 22. In the embodiment, the heat pipe 22 includes a first contact surface 221 and a second contact surface 222, the microprocessor 16 is located at the first contact surface 221, so that the first contact surface 221 is connected to the heat-generating surface of the microprocessor 16. The first actuator 21 and the at least one cooling chip 20 are disposed and located at the second contact surface 222 to perform heat convection of the heat dissipation liquid 23 inside the heat pipe 22, so that the convective heat exchange from the heat source of the microprocessor 16 can be accelerated by the heat pipe 22. In another embodiment, as shown in FIG. 5B, the microprocessor 16 and the at least one cooling chip 20 are located at the first contact surface 221, and the microprocessor 16 and the at least one cooling chip 20 are connected to the first contact surface 221 of the heat pipe 22. The positioning accommodation seat 25 is disposed and positioned at the second contact surface 222 of the heat pipe 22. Moreover, the positioning accommodation 25 includes a vent hole 251 disposed thereon, and the first actuator 21 is disposed and positioned inside the positioning accommodation 25 for actuating and transporting the gas through the vent hole 251 to exchange heat with the heat pipe 22. As shown in FIG. 5A, the arrow indicates that the heat generated from the microprocessor 16 is transferred and led out through the heat dissipation processing module 2. In the embodiment, the heat dissipation processing 2 further includes a liquid pump 24, and the liquid pump 24 is in fluid communication with an interior space of the heat pipe 22. Whereby, the heat dissipation liquid 23 in the heat pipe 22 can be pumped and circulated, and the heat exchange effect of the heat pipe 22 is thus accelerated.

Figure 5C:
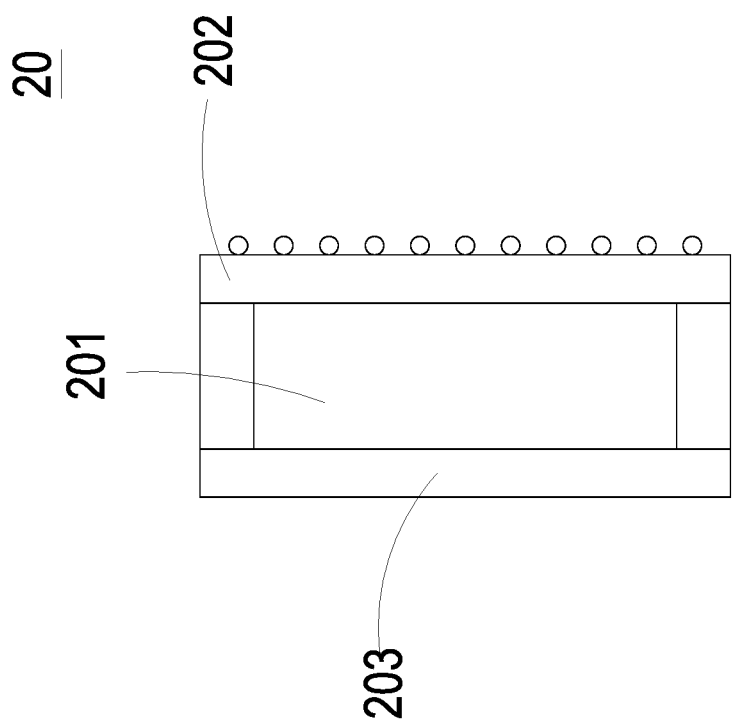
FIG. 5C is a schematic view illustrating a cooling chip of the wearable display device according to the embodiment of the present disclosure.
Figure 6:
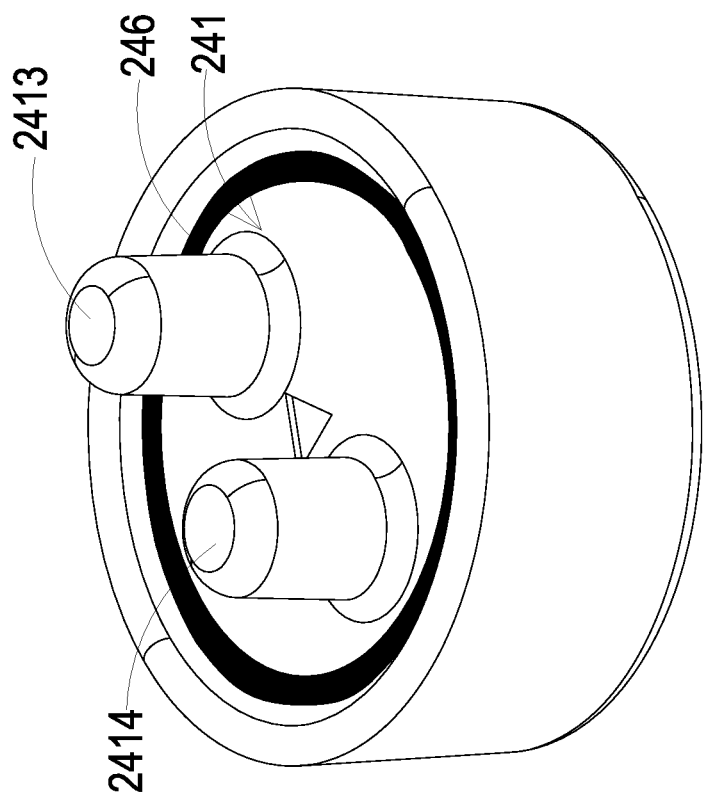
FIG. 6 is a schematic view illustrating a liquid pump of the wearable display device according to the embodiment of the present disclosure.
Figure 7:
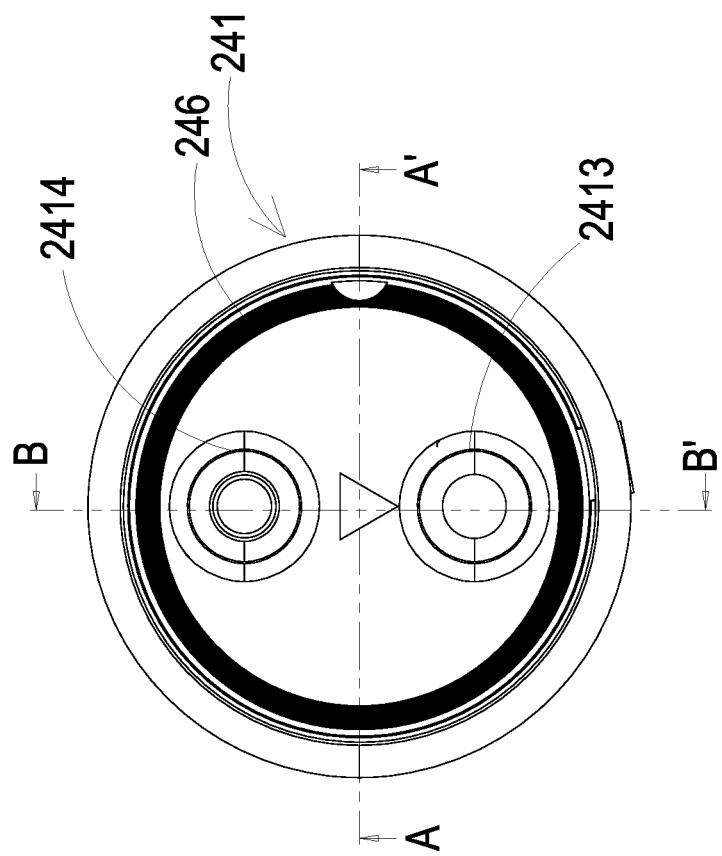
FIG. 7 is a top view illustrating the liquid pump of the wearable display device according to the embodiment of the present disclosure.
Figure 8A:
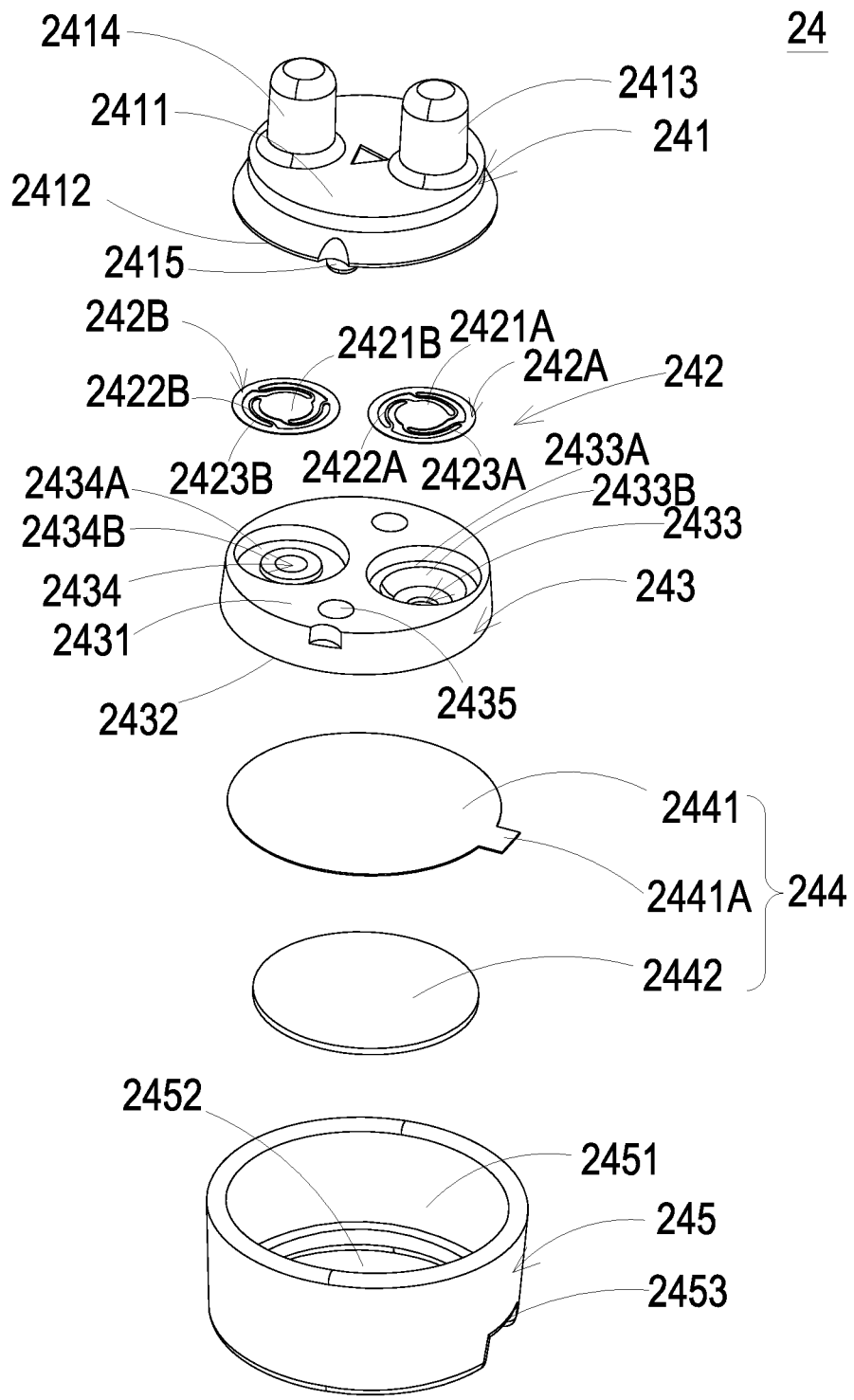
FIG. 8A is a schematic exploded view illustrating the liquid pump of the wearable display device according to the embodiment of the present disclosure.
Figure 8B:
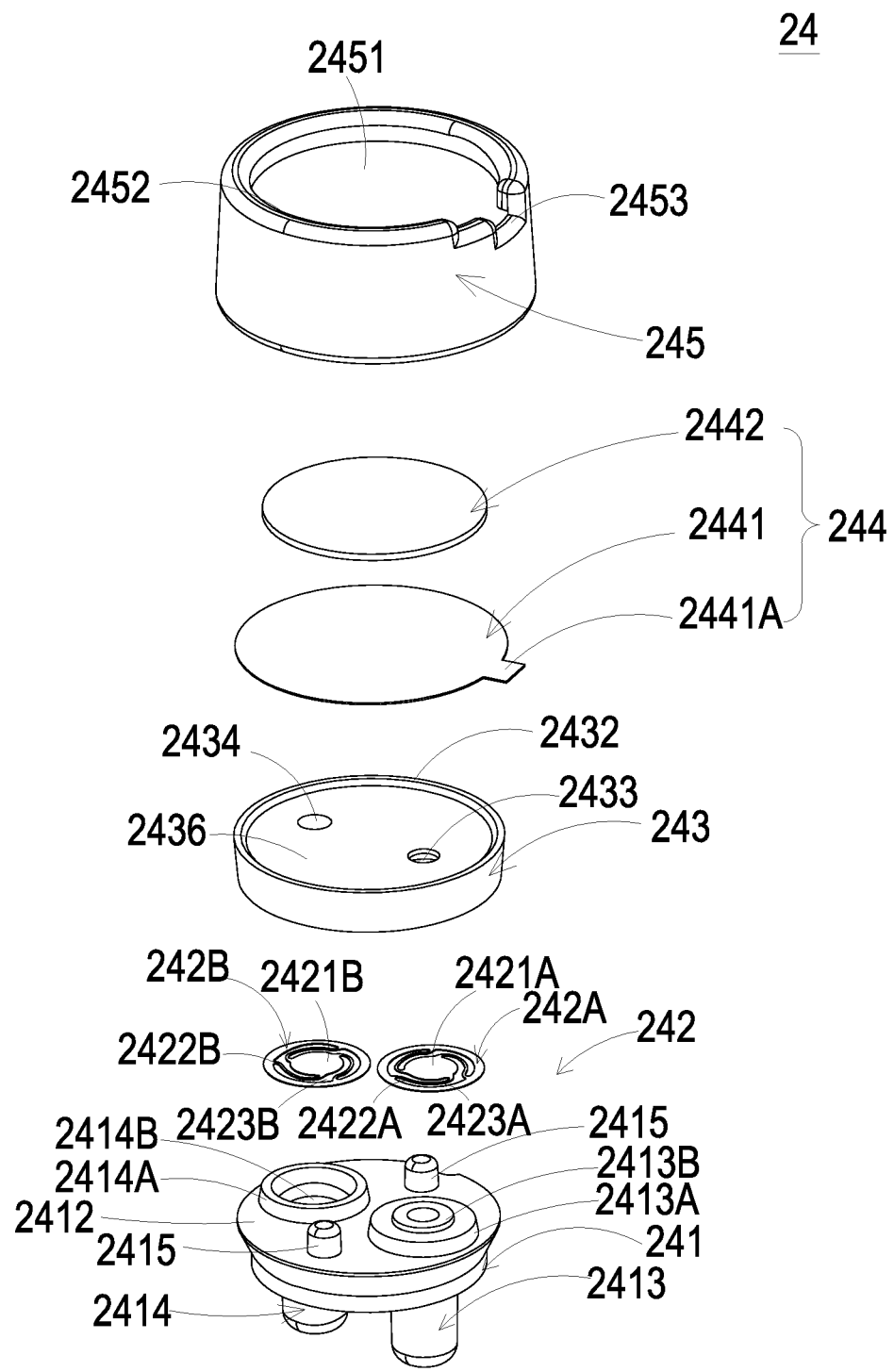
FIG. 8B is a schematic exploded view illustrating the liquid pump of the wearable display device according to the embodiment of the present disclosure from another angle.

Please refer to FIG. 5A and FIG. 5C. FIG. 5C is a schematic structure of the cooling chip 20. The cooling chip 20 includes a refrigeration unit 201, a cooling surface 202 and a heating surface 203. The cooling surface 202 is disposed opposite to the heating surface 203. The refrigeration unit 201 is integrally sandwiched and packaged between the cooling surface 202 and the heating surface 203 to form the cooling chip 20. In the embodiment, the cooling surface 202 of the cooling chip 20 is connected to the heat pipe 22 to exchange heat with the heat pipe 22, so as to reduce the temperature of the heat pipe 22 and the heat dissipation liquid 23, and then dissipate the heat from the heat surface 203 s to achieve the cooling effect.

As for the structure and operation steps of the liquid pump 24, is described as follows. Please refer to FIGS. 6, 7, 8A, 8B, 9, 10, 11A and FIG. 11B. In the embodiment, the liquid pump 24 includes a valve cover body 241, two valve plates 242, a valve base seat 243, an actuator 244 and an outer sleeve 245. The valve cover body 241 includes a valve-cover first surface 2411, a valve-cover second surface 2412, an inlet passage 2413, an outlet passage 2414 and a plurality of latch elements 2415. Each of the inlet passage 2413 and the outlet passage 2414 runs through the valve-cover first surface 2411 and the valve-cover second surface 2412. An inlet protrusion platform 2413A surrounding the outer edge of the inlet passage 2413 protrudes from the valve-cover second surface 2412, and a first convex structure 2413B is formed on the inlet protrusion platform 2413A. An outlet protrusion platform 2414A surrounding the outer edge of the outlet passage 2414 protrudes from the valve-cover second surface 2412, and an outlet chamber 2414B is concavely formed on the center of the outlet protrusion platform 2414A. Moreover, the plurality of latch element 2415 protrude outwardly from the valve-cover second surface 2412. In the embodiment, the two valve plates 242 include a first valve plate 242A and a second valve plate 242B. The first valve plate 242A includes a central valve disc 2421A, and the second valve plate 242B includes a central valve disc 2421B. A plurality of extension parts 2422A are disposed around the central plate disc 2421A, and a plurality of extension parts 2422B are disposed around the central valve disc 2421B for elastically supporting. At least one hollow hole 2423A is formed between each of two adjacent extension parts 2422A, and at least one hollow hole 2423B is formed between each of two adjacent extension parts 2422B. In the embodiment, the valve base seat 243 corresponds to and is connected to the valve cover body 241. The first valve plate 242A and the second valve plate 242B are disposed and positioned between the valve cover body 241 and the valve base seat 243. The valve base seat 243 includes a valve-base first surface 2431, a valve-base second surface 2432, an inlet valve channel 2433 and an outlet valve channel 2434. Each of the inlet valve channel 2433 and the outlet valve channel 2434 runs through the valve-base first surface 2431 and the valve-base second surface 2432. An inlet recessed platform 2433A surrounding the inner edge of the inlet valve channel 2433 is concavely formed from the valve-base first surface 2431 for matching and connecting with the inlet protrusion platform 2413A of the valve cover body 241. The first valve plate 242A is disposed between the inlet recessed platform 2433A and the inlet protrusion plate 2413A, so that the central valve disc 2421A is abutted against with the first convex structure 2413B of the valve cover body 241 to seal the inlet passage 2413 of the valve cover body 241. Moreover, an inlet chamber 2433B is concavely formed at the center of the recessed platform 2433A. An outlet recessed platform 2434A surrounding the inner edge of the outlet valve channel 2434 is concavely formed from the valve-base first surface 2431, and a second convex structure 2434B protrudes from the center of the outlet recessed platform 2434A. The outlet recessed platform 2434A and the outlet protrusion plate 2414A of the valve cover body 241 are connected to each other. The second valve plate 242B is disposed between the outlet recessed platform 2434A and the outlet protrusion plate 2414A, so that the central valve disc 2421B is abutted against with the second convex structure 2433B to seal the outlet valve channel 2434 of the valve base seat 243. In addition, the vale base seat 243 further includes a plurality of engaging holes 2435 disposed on the valve-base first surface 2431 and the plurality of engaging holes 2435 is corresponding to the positions of the plurality of latch elements 2415. The valve base seat 243 and the valve cover body 241 are connected to seal the first valve plate 242A and the second valve plate 242B, and achieve the positioning and assembling effect. In addition, a collecting chamber 2436 is concavely formed on the valve-base second surface 2432, and in fluid communication with the inlet valve channel 2433 and the outlet valve channel 2434. In the embodiment, the actuator 244 includes a vibration plate 2441 and a piezoelectric unit 2442. The piezoelectric unit 2442 is attached to one side of the vibration plate 2441. The vibration plate 2441 has an electrical pin 2441A. The vibration plate 2441 covers the valve-base second surface 2432 of the valve base seat 243, so as to seal the collecting chamber 2436. In the embodiment, the outer sleeve 245 is recessed on one side with an inner wall recessed space 2451. The bottom of the inner wall recessed space 2451 has a hollowed-out central groove 2452 and a penetrating frame opening 2453 penetrating one side of the outer sleeve 245 and in fluid communication with the outside. The actuator 244, the valve base seat 243, the two valve plates 242 and the valve cover body 241 are placed in the inner wall recessed space 2451 sequentially, and the electrical pin 2441A of the actuator 244 runs through the penetrating frame opening 2453, and the sealing adhesive 246 is filled into the inner wall recessed space 2451 for positioning. The piezoelectric element 2442 of the actuator 244 is correspondingly disposed in the central groove 2452, so as to vibrate and displace in the central groove 2452 when the piezoelectric element 2442 is driven. The inlet passage 2413 of the valve cover body 241 is corresponding to the inlet chamber 2433B of the valve base seat 243, and the fluid communication therebetween is controlled by the first valve plate 242A. The outlet chamber 2414B of the valve cover body 241 is corresponding to the outlet valve channel 2434 of the valve base seat 243, and the fluid communication therebetween is controlled by the second valve plate 242B. The first convex structure 2413B of the valve cover body 241 abuts against the central valve disc 2421A of the first valve plate 242A to seal the inlet passage 2413 of the valve cover body 241, so as to generate a pre-force effect to avoid the backflow. The second convex structure 2434B of the valve base seat 243 abuts against the central valve disc 2421B of the second valve plate 242B to seal the outlet valve channel 2434 of the valve base seat 243, so as to generate a pre-force effect to avoid the back flow. When the piezoelectric unit 2442 of the actuator 244 is vibrated and displaced downwardly, a suction force is generated in the inlet chamber 2433B of the valve base seat 243, so that the central valve disc 2421A of the first valve plate 242A is pulled and displaced and doesn't seal the inlet passage 2413 of the valve cover body 241, therefore, the fluid is drawn through the inlet passage 2413 of the valve cover body 241, transported through the hollow hole 2423A of the first valve plate 242A, flowed into the inlet chamber 2433B of the valve base seat 243, and flowed into the collecting chamber 2436 to collect the liquid temporarily. When the piezoelectric unit 2442 of the actuator 244 is vibrated and displaced upwardly, the temporarily collected liquid in the collecting chamber 2436 is pushed toward the outlet valve channel 2434 of the valve base seat 243, and makes the central valve disc 2421B of the second valve plate 242B separated from abutting state of the second convex structure 2434B, so as to allow the fluid flows smoothly into the outlet chamber 2414B of the valve cover body 241 through the hollow hole 2423B of the second valve plate 242B, and then flows out through the outlet passage 2414 to achieve the liquid transportation.

As shown in FIGS. 6, 7, 8A and FIG. 8B, the liquid pump 24 includes a valve cover body 241, two valve plates 242, a valve base seat 243, an actuator 244 and an outer sleeve 245. The actuator 244, the valve base seat 243, two valve plates 242 and the valve cover body 241 are sequentially stacked in the outer sleeve 245, and then a sealing adhesive 246 is used to seal the outer sleeve 245 and position the internal components, so as to assemble the liquid pump 24.

As shown in FIG. 6, FIG. 8A, FIG. 8B and FIG. 10, the valve cover body 241 includes a valve-cover first surface 2411, a valve-cover second surface 2412, an inlet passage 2413, an outlet passage 2414 and a plurality of latch elements 2415. Each of the inlet passage 2413 and the outlet passage 2414 runs through the valve-cover first surface 2411 and the valve-cover second surface 2412. An inlet protrusion platform 2413A surrounding the outer edge of the inlet passage 2413 protrudes from the valve-cover second surface 2412, and a first convex structure 2413B is formed on the inlet protrusion platform 2413A. An outlet protrusion platform 2414A surrounding the outer edge of the outlet passage 2414 protrudes from the valve-cover second surface 2412, and an outlet chamber 2414B is concavely formed on the center of the outlet protrusion platform 2414A. Moreover, the plurality of latch elements 2415 protrude outwardly from the valve-cover second surface 2412. In the embodiment, the number of the latch elements 2415 is exemplified by two correspondingly, but not limited thereto. The number is adjustable according to the practical positioning requirements.

In the embodiment, the two valve plates 242 made of polyimide (PI) are produced by a reactive ion etching (RIE) process, respectively. That is, a photosensitive photoresist is applied to a valve structure for the valve plate 242, a pattern for the valve plate 242 is formed after exposure and development. Since the polyimide layer covered by the photoresist is protected from etching, the valve structure of the valve plate 242 is etched to form the two valve plates 242. In the embodiment, the valve plates 242 include a first valve plate 242A and a second valve plate 242B. The first valve plate 242A includes a central valve disc 2421A, and the second valve plate 242B includes a central valve disc 2421B. A plurality of extension parts 2422A are disposed around the central plate disc 2421A, and a plurality of extension parts 2422B are disposed around the central plate disc 2421B for elastically supporting. At least one hollow hole 2423A is formed between each of two adjacent extension parts 2422A, and at least one hollow hole 2423B is formed between each of two adjacent extension parts 2422B.

Figure 9:
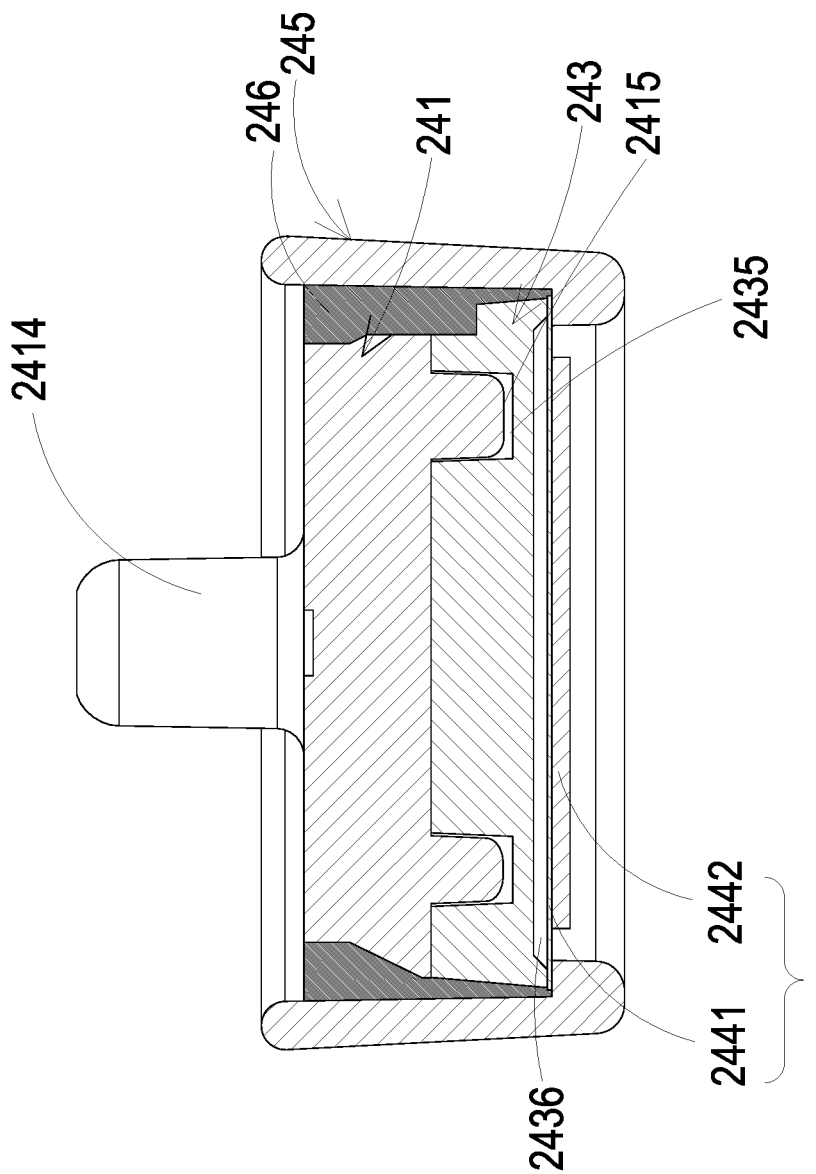
FIG. 9 is a cross sectional view taken along the line AA' in FIG. 7.
Figure 10:
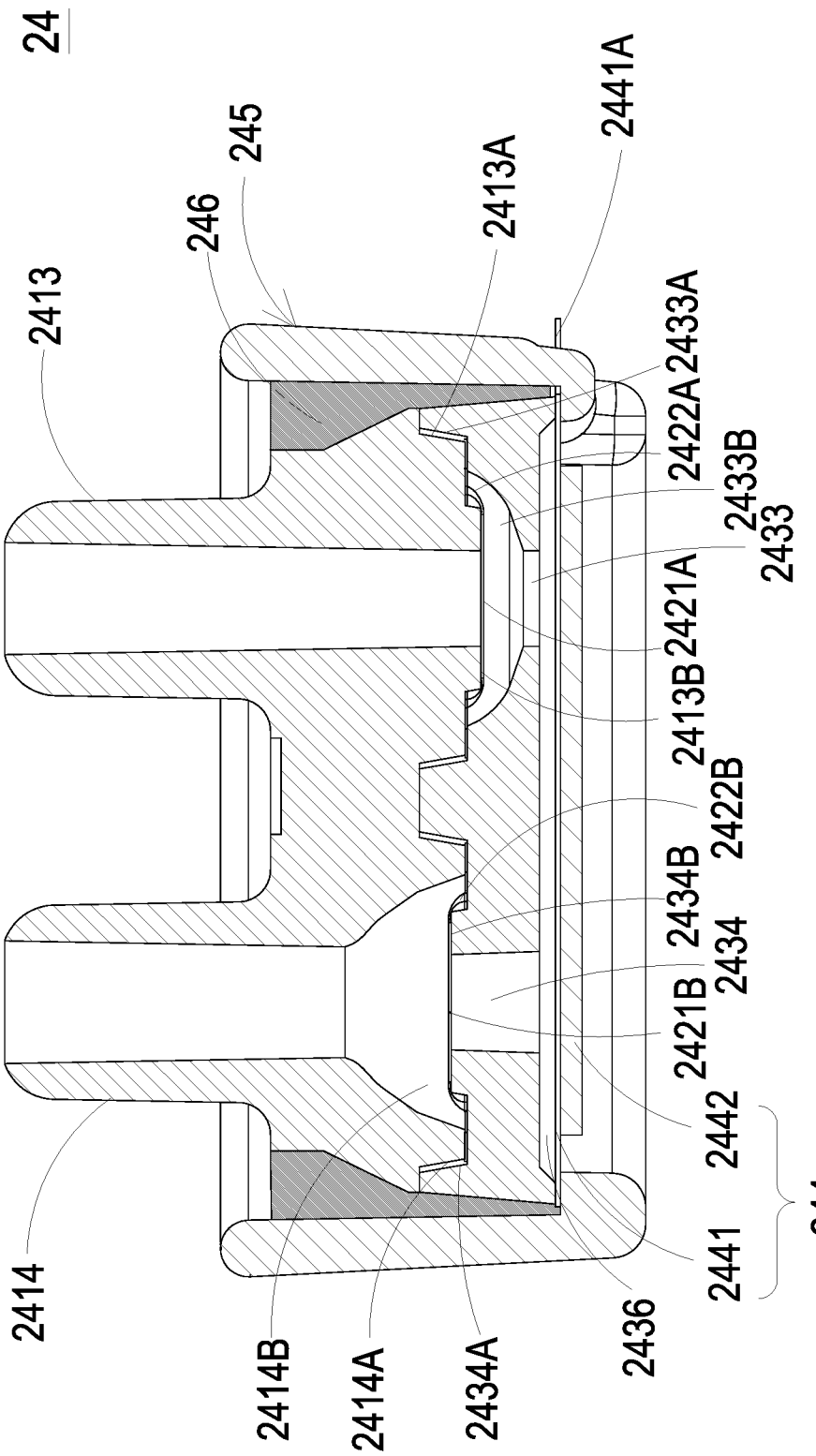
FIG. 10 is a cross sectional view taken along the line BB' in FIG. 7.

In the embodiment, the valve base seat 243 and the valve cover body 241 are assembled with each other, and the first valve plate 242A and the second valve plate 242B are disposed and positioned between the valve base seat 243 and the valve cover body 241. The valve base seat 243 includes a valve-base first surface 2431, a valve-base second surface 2432, an inlet valve channel 2433 and an outlet valve channel 2434. Each of the inlet valve channel 2433 and the outlet valve channel 2434 runs through the valve-base first surface 2431 and the valve-base second surface 2432. An inlet recessed platform 2433A surrounding the inner edge of the inlet valve channel 2433 is concavely formed from the valve-base first surface 2431 for connecting with inlet protrusion platform 2413A of the valve cover body 241. The first valve plate 242A is disposed between the inlet recessed platform 2433A and the inlet protrusion plate 2413A, so that the central valve disc 2421A is abutted against with the first convex structure 2413B of the valve cover body 241 to seal the inlet passage 2413 of the valve cover body 241. The central valve disc 2421A of the first valve plate 242A constantly abuts against the first convex structure 2413B to generate a pre-force effect, which helps the first valve plate 242A to be tightly seal up on the first convex structure 2413B and thus avoids the backflow, as shown FIG. 10. Moreover, an inlet chamber 2433B is concavely formed at the center of the recessed platform 2433A. An outlet recessed platform 2434A surrounding the inner edge of the outlet valve channel 2434 is concavely formed from the valve-base first surface 2431, and a second convex structure 2434B protrudes from the center of the outlet recessed platform 2434A. The outlet recessed platform 2434A and the outlet protrusion plate 2414A of the valve cover body 241 are connected to each other. The second valve plate 242B is disposed between the outlet recessed platform 2434A and the outlet protrusion plate 2414A, so that the central valve disc 2421B is abutted against with the second convex structure 2433B to seal the outlet valve channel 2434 of the valve base seat 243. The central valve disc 2421B of the second valve plate 242B constantly abuts against the second convex structure 2434B to generate a pre-force effect, which helps the second valve plate 242B to be tightly seal up on the second convex structure 2434B and thus avoids the backflow, as shown FIG. 10. In addition, the vale base seat 243 further includes a plurality of engaging holes 2435 disposed on the valve-base first surface 2431 and the plurality of engaging holes 2435 is corresponding to the positions of the plurality of latch elements 2415 with the same number. In that, as shown in FIG. 9, the plurality of latch elements 2415 of the valve cover body 241 are correspondingly inserted into and engaged with the plurality of engaging holes 2435 of the valve base seat 243, so that the valve base seat 243 and the valve cover body 241 are connected to seal the first valve plate 242A and the second valve plate 242B, and achieve the positioning and assembling effect. In the embodiment, the number of the latch elements 2415 is exemplified by two, and the number of the engaging holes 2435 is also exemplified by two, but not limited thereto. The numbers of the latch elements 2415 and the engaging holes 2435 are adjustable according to the actual positioning requirements. In addition, a collecting chamber 2436 is concavely formed on the valve-base second surface 2432, and the collecting chamber 2436 is in fluid communication with the inlet valve channel 2433 and the outlet valve channel 2434.

In the embodiment, the actuator 244 includes a vibration plate 2441 and a piezoelectric unit 2442. The vibration plate 2441 is made of metal, and the piezoelectric unit 2442 is made of lead-zirconate-titanate (PZT) type piezoelectric powder with high piezoelectric constant. In the embodiment, the piezoelectric unit 2442 is attached to one side of the vibration plate 2441, and the vibration plate 2441 covers the valve-base second surface 2432 of the valve base seat 243, so as to seal the collecting chamber 2436. Moreover, the vibration plate 2441 has an electrical pin 2441A for external electrical connection with the power source, so that the piezoelectric element 2442 can be driven to deform for vibration and displacement.

In the embodiment, the outer sleeve 245 is recessed on one side with an inner wall recessed space 2451, and the bottom of the inner wall recessed space 2451 has a hollowed-out central groove 2452 and a penetrating frame opening 2453 penetrating one side of the outer sleeve 245 and in fluid communication with the outside. The actuator 244, the valve base seat 243, the two valve plates 242 and the valve cover body 241 are placed in the inner wall recessed space 2451 sequentially, and the electrical pin 2441A of the actuator 244 runs through the penetrating frame opening 2453, and the sealing adhesive 246 is filled in the inner wall recessed space 2451 for positioning, and the piezoelectric element 2442 of the actuator 244 is correspondingly disposed in the central groove 2452, so as to vibrate and displace in the central groove 2452 as the piezoelectric element 2442 been driven.

Figure 11A:
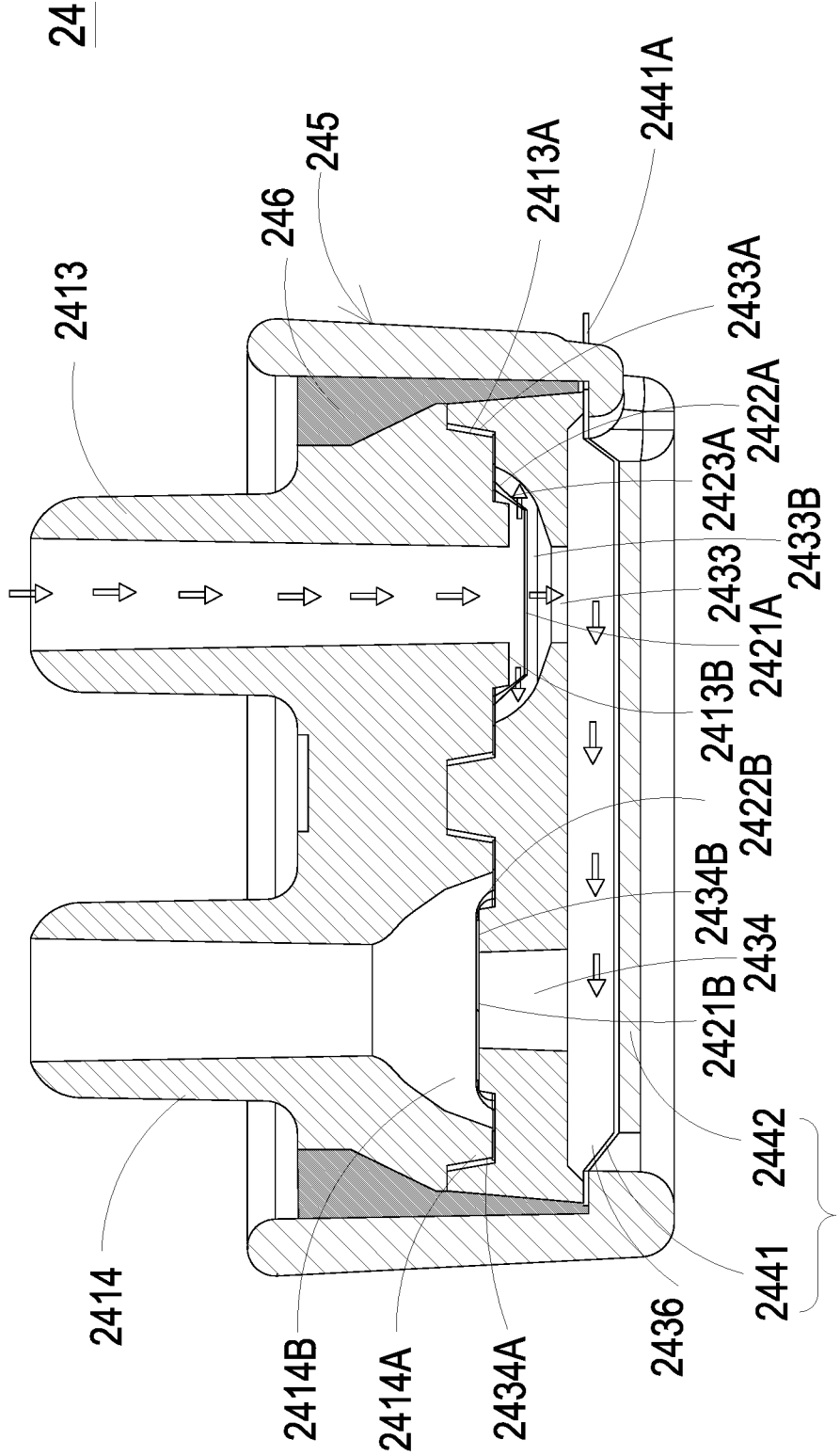
FIGS. 11A to 11B schematically illustrate the operation steps of the liquid pump of the wearable display device according to the embodiment of the present disclosure.
Figure 11B:
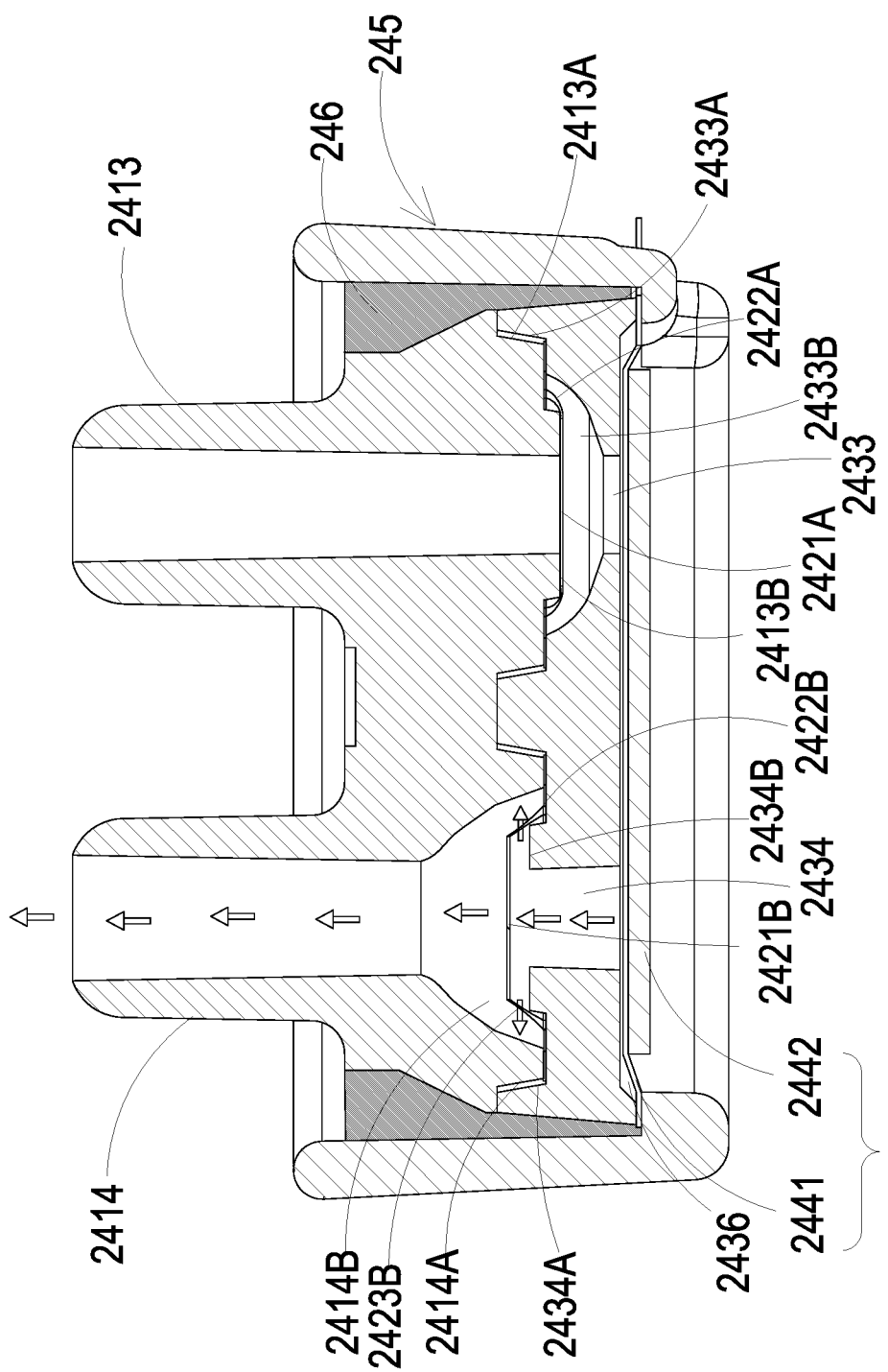

The operation steps of the micro liquid pump 24 for performing the fluid transportation is illustrated in FIG. 11A and FIG. 11B. As shown in FIG. 11A, when the piezoelectric unit 2442 is driven by applying a voltage to shift and displace downwardly, a suction force is generated in the inlet chamber 2433B of the valve base seat 243, so that the central valve disc 2421A of the first valve plate 242A is pulled to displace. At this time, the central valve disc 2421A of the first valve plate 242A doesn't seal the inlet passage 2413 of the valve cover body 241, the fluid is drawn through the inlet passage 2413 of the valve cover body 241, transported through the hollow hole 2423A of the first valve plate 242A, flowed into the inlet chamber 2433B of the valve base seat 243, and flowed into the collecting chamber 2436 to collect the liquid temporarily. Thereafter, as shown in FIG. 11B, the piezoelectric unit 2442 of the actuator 244 is vibrated and displaced upwardly, and the temporarily collected liquid in the collecting chamber 2436 is pushed toward the outlet valve channel 2434 of the valve base seat 243. In that, the central valve disc 2421B of the second valve plate 242B is separated from abutting state of the second convex structure 2434B. The fluid flows smoothly into the outlet chamber 2414B of the valve cover body 241 through the hollow hole 2423B of the second valve plate 242B, and then flows out through the outlet passage 2414 to achieve the liquid transportation.

Please refer to FIGS. 2A, 2B, 3 and 4. In the embodiment, the inflatable actuation module 3 is disposed on the circuit board 15. The inflatable actuation module 3 includes a base 31, a ventilation channel 32, a second actuator 33 and a valve component 34. The base 31 is positioned at the circuit board 15 and in fluid communication with the ventilation channel 32. The second actuator 33 is positioned in the base 31. The ventilation channel 32 is in fluid communication with the inflatable airbag 13. The valve component 34 capable of being opened or closed is disposed on the base 31 and covers the second actuator 33. In that, the valve component 34 is driven to be opened or closed for controlling the air introduction of the second actuator 33. Notably, when the second actuator 33 and the valve component 34 are driven, the valve component 34 is opened to control the air introduction of the second actuator 33, and the second actuator 33 is enabled at the same time, whereby the gas is transported through the ventilation channel 32 and inflated the inflatable airbag 13. Thus, the main body 1 can be firmly fitted and positioned on the head of the wearer, to improve the comfortability while wearing.

Figure 16A:
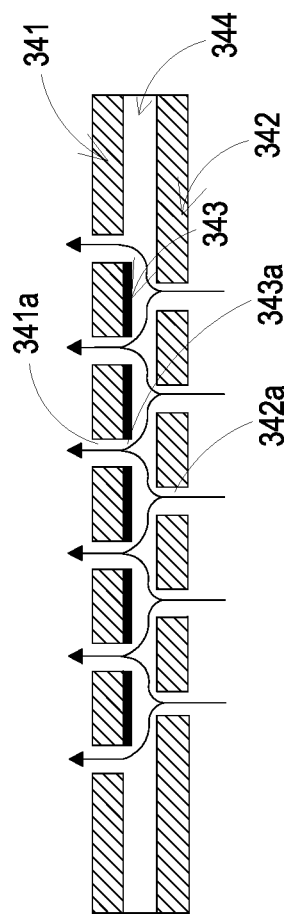
FIG. 16A is a cross sectional view illustrating the valve component in the opened state according to the embodiment of the present disclosure.
Figure 16B:
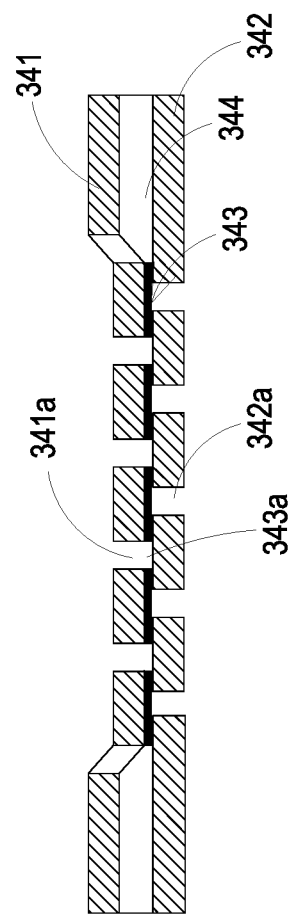
FIG. 16B is a cross sectional view illustrating the valve component in the closed state according to the embodiment of the present disclosure.
Figure 17A:
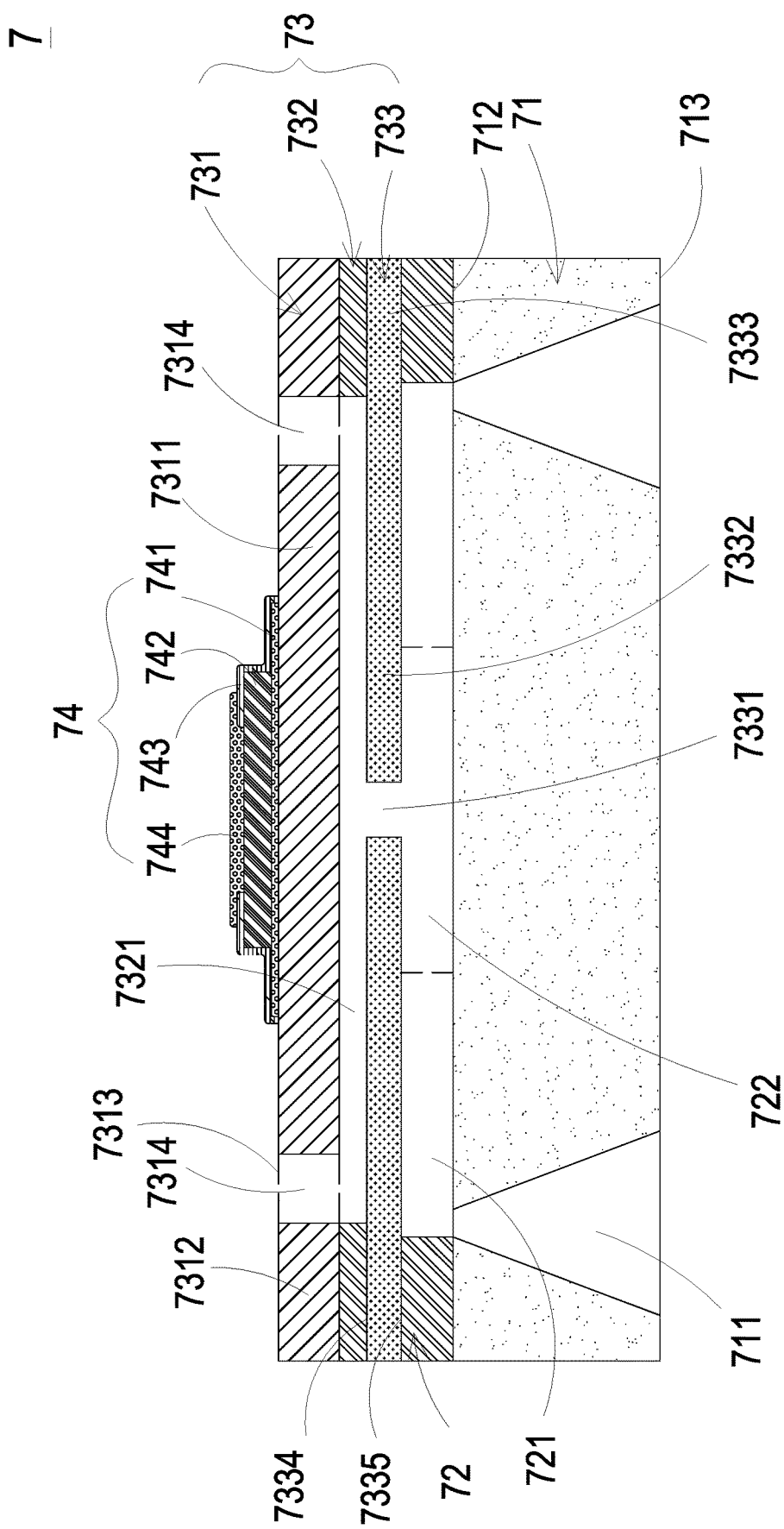
FIG. 17A is a cross sectional view illustrating a microelectromechanical-system micro pump of the wearable display device according to the embodiment of the present disclosure.
Figure 17B:
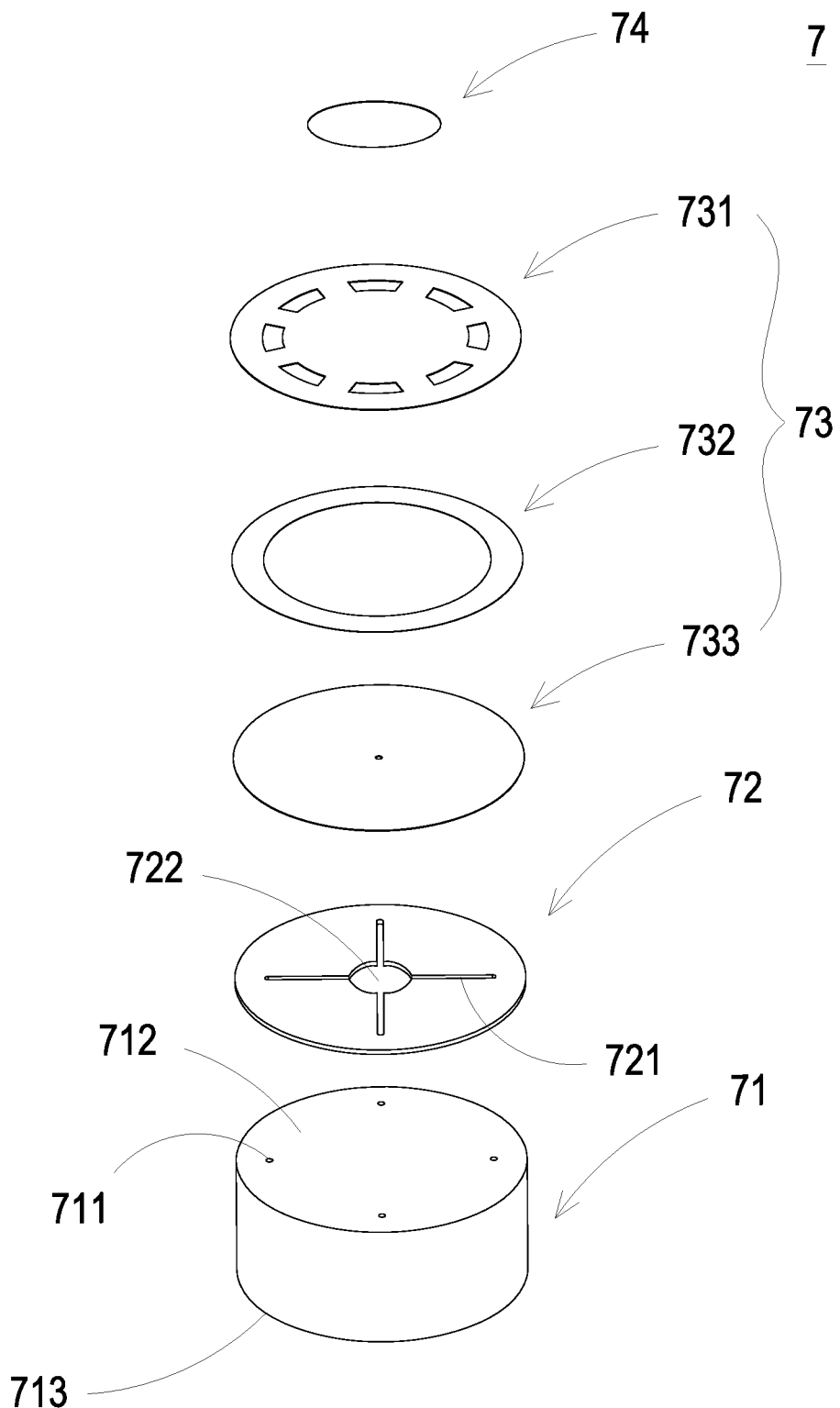
FIG. 17B is a schematic exploded view illustrating the microelectromechanical-system micro pump of the wearable display device according to the embodiment of the present disclosure.

The opened state and closed state of the valve component 34 are shown in FIG. 16A and FIG. 16B. In the embodiment, the valve component 34 includes a valve conductive element 341, a valve base 342 and a sealing element 343. The valve conductive element 341 formed by a charged piezoelectric material is electrically connected to the circuit board 15 to receive a driving signal and deform. An accommodation space 344 is maintained between the valve conductive element 341 and the valve base 342. The sealing element 343 made of a flexible material is attached to one side of the valve conductive element 341 and placed in the accommodation space 344. A plurality of through holes 341a, 342a, 343a are formed on the valve conductive element 341, the valve base 342 and the sealing element 343, the through hole 341a of the valve conductive element 341 and the through hole 343a of the sealing element 343 are aligned to each other, and the through hole 342a of the valve base 342 and the through hole 341a of the valve conductive element 341 are misaligned to each other. As shown in FIG. 16A, when the valve conductive element 341 does not receive the driving signal from the microprocessor 16, the valve conductive element 341 is maintained in the accommodation space 344 and form a distance from the valve base 342, so that the valve component 34 is opened since the through hole 342a of the valve base 342 and the through hole 341a of the valve conductive element 341 are misaligned to each other. As shown in FIG. 16B, when the valve conductive element 341 receives the driving signal from the microprocessor 16, the valve conductive element 341 is deformed and attached to the valve base 342, the through hole 342a of the valve base 342 is sealed by the sealing component 343 since the through hole 343a of the sealing element 343 and the through hole 342a of the valve base 342 are misaligned to each other, so that the valve component 34 is closed.

Figure 3:
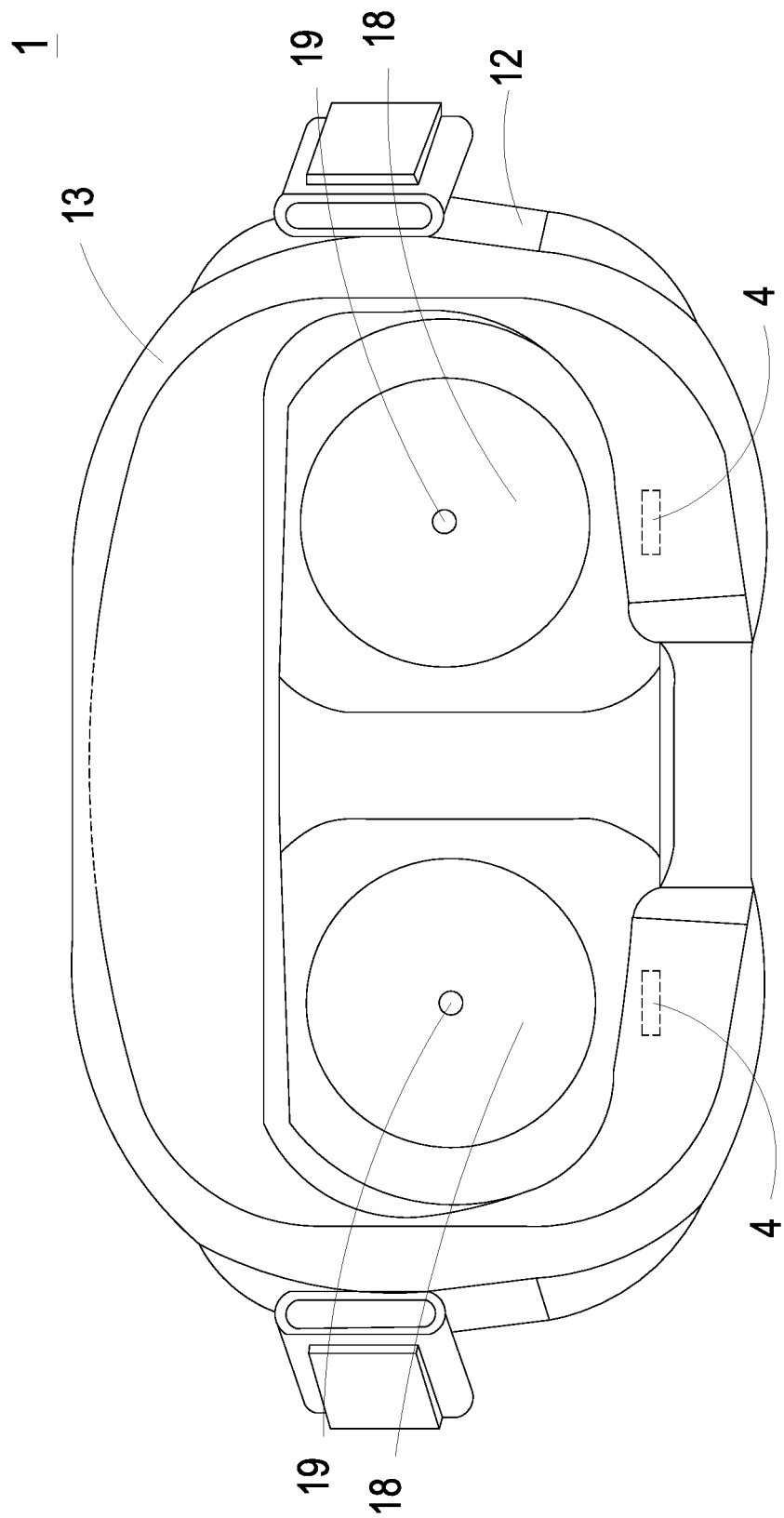
FIG. 3 is schematic view of the wearable display device of the present disclosure from another angle.
Figure 4:
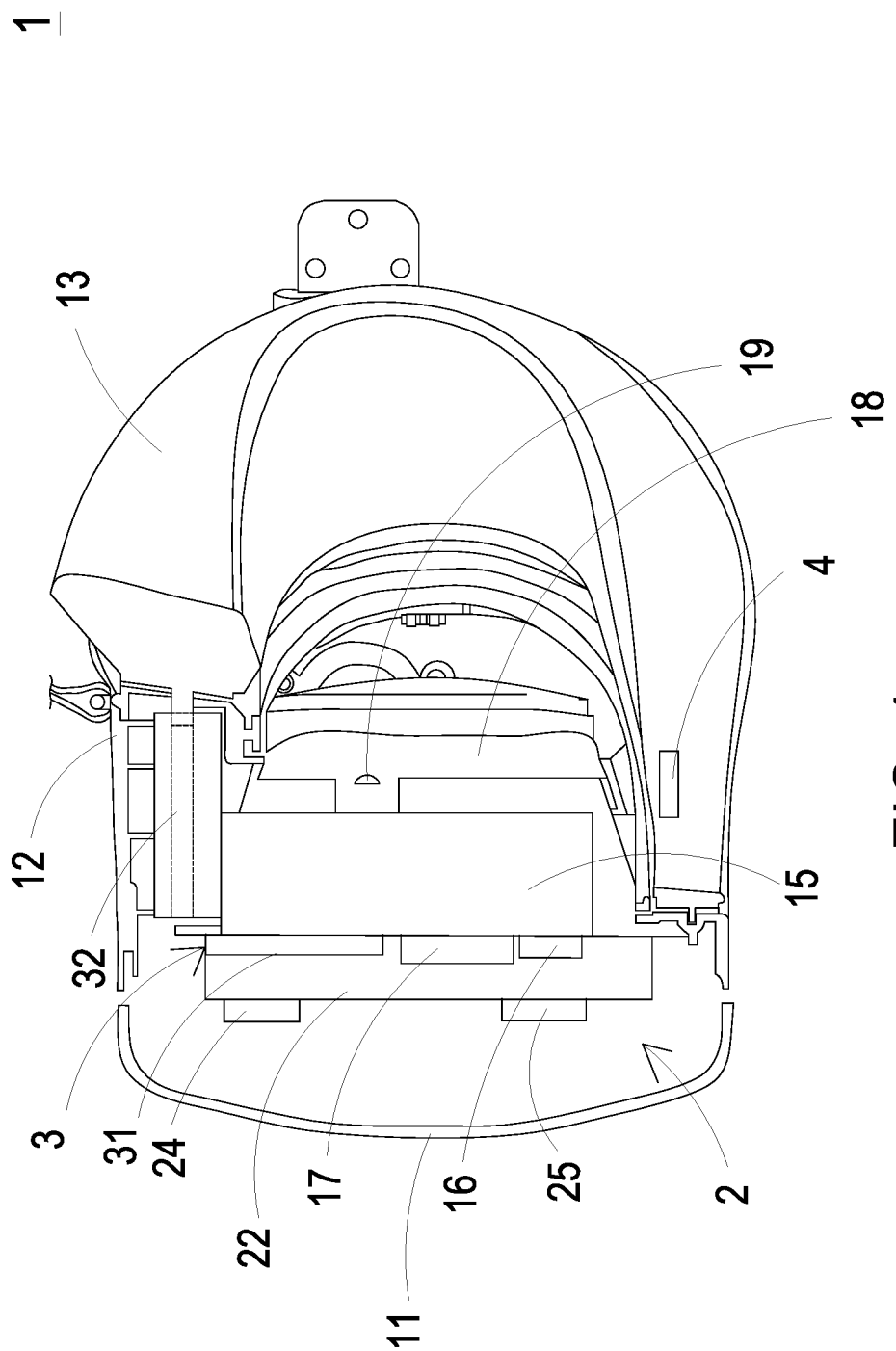
FIG. 4 is a cross sectional view illustrating the wearable display device according to the embodiment of the present disclosure.

Please refer to FIG. 3 and FIG. 4. In the embodiment, the main body 1 further includes at least one intraocular pressure sensor 19 and at least one third actuator 4 to constitute an intraocular pressure detection device. The at least one intraocular pressure sensor 19 is disposed at the center point of the at least one display 18 and electrically connected to the circuit board 15 for emitting an infrared light and detecting the light energy of the reflected infrared light. The at least one third actuator 4 is disposed under the at least one display 18 and electrically connected to the circuit board 15 for generating a pulsed gas. Notably, the at least one intraocular pressure sensor 19 can be two separated intraocular pressure sensors 19 disposed in the lateral cover 12, respectively, but not limited thereto. Preferably but not exclusively, the at least one intraocular pressure sensor 19 includes a pair of intraocular pressure sensors disposed in the lateral cover 12. Similarly, the at least one third actuator 4 can be two separated third actuators 4 disposed under the display 18, respectively, but not limited thereto. Preferably but not exclusively, the at least one third actuator 4 might also be a pair of the third actuators 4 disposed under the display 18. When the at least one third actuator 3 is driven to generate the pulsed gas, the at least one intraocular pressure sensor 19 emits the infrared light, and calculates the light energy reflected from the infrared light to detect an intraocular pressure data of a wearer, so that the wearable display device 1 is allowed to display the intraocular pressure data and issue a notification message. Notably, the principle of the measurement of intraocular pressure is to use the pulsed gas to hit the surface of the cornea. The force of the pulsed air would increase over time, to cause the cornea to be flattened or even slightly sunken. When the pulsed gas hits the cornea, the surface of the cornea is forced to deform from convex to flat and then concave. When the impact of the pulsed gas is decreased, the surface of the cornea is deformed gradually from concave to flat, and then returns to the original shape. During the impact time of the pulsed gas on the cornea, for example within 20 milliseconds, the infrared light is emitted to detect the light energy reflected by the cornea from the infrared light, so as to determine the depression degree of corneal. Since different curvatures make different reflection angle of the infrared light, and the reflected light energy is also different, such that the wearer's intraocular pressure can be obtained after calculation. In addition, notably, after the microprocessor 16 obtains the wearer's intraocular pressure data, the value can be displayed on the display 18. When the wearer's intraocular pressure data is not within a normal range, the wearer can be warned by issuing a notification message on the display 18. The warning procedure can include temporarily turn off the display 18 after a few seconds, so as to force the wearer to rest. It can also include flashing the screen of the display 18 or reminding the wearer by sound or voice, so as to remind the wearer to take care of the eye health and not to excessive use of the eyes which causing dizziness or excessive intraocular pressure that is harmful to health.

In the embodiment, the first actuator 21, the second actuator 33, and the third actuator 4 can be, for example but not limited to, a micro pump or a blower-type micro pump or a microelectromechanical-system micro pump, respectively. The structures and gas transportation operation steps of the micro pump, the blower-type micro pump and microelectromechanical-system micro pump are sequentially described below.

As shown in FIGS. 12A, 12B, 13A to 13E, the structure of the micro pump 5 is illustrated. In the embodiment, the micro pump 5 includes an inlet plate 51, a resonance plate 52, a piezoelectric actuator 53, a first insulation plate 54, a conductive plate 55 and a second insulation plate 56 stacked sequentially. The inlet plate 51 has at least one inlet aperture 511, at least one convergence channel 512 and a convergence chamber 513. The at least one inlet aperture 511 is disposed to inhale the gas, and is corresponding to the at least one convergence channel 512 and in fluid communication with the at least one convergence channel 512. The at least one convergence channel 512 is converged toward the convergence chamber 513, so as to guide the gas inhaled from the inlet aperture 511 to the convergence chamber 513. In the embodiment, the numbers of the inlet apertures 511 and the convergence channels 512 are the same. In the embodiment, the numbers of the inlet apertures 511 and the convergence channels 512 are exemplified by four, but not limited thereto. The four inlet apertures 511 are in fluid communication with the four convergence channels 512, respectively, and the four convergence channels 512 are converged toward the convergence chamber 513.

Figure 12A:
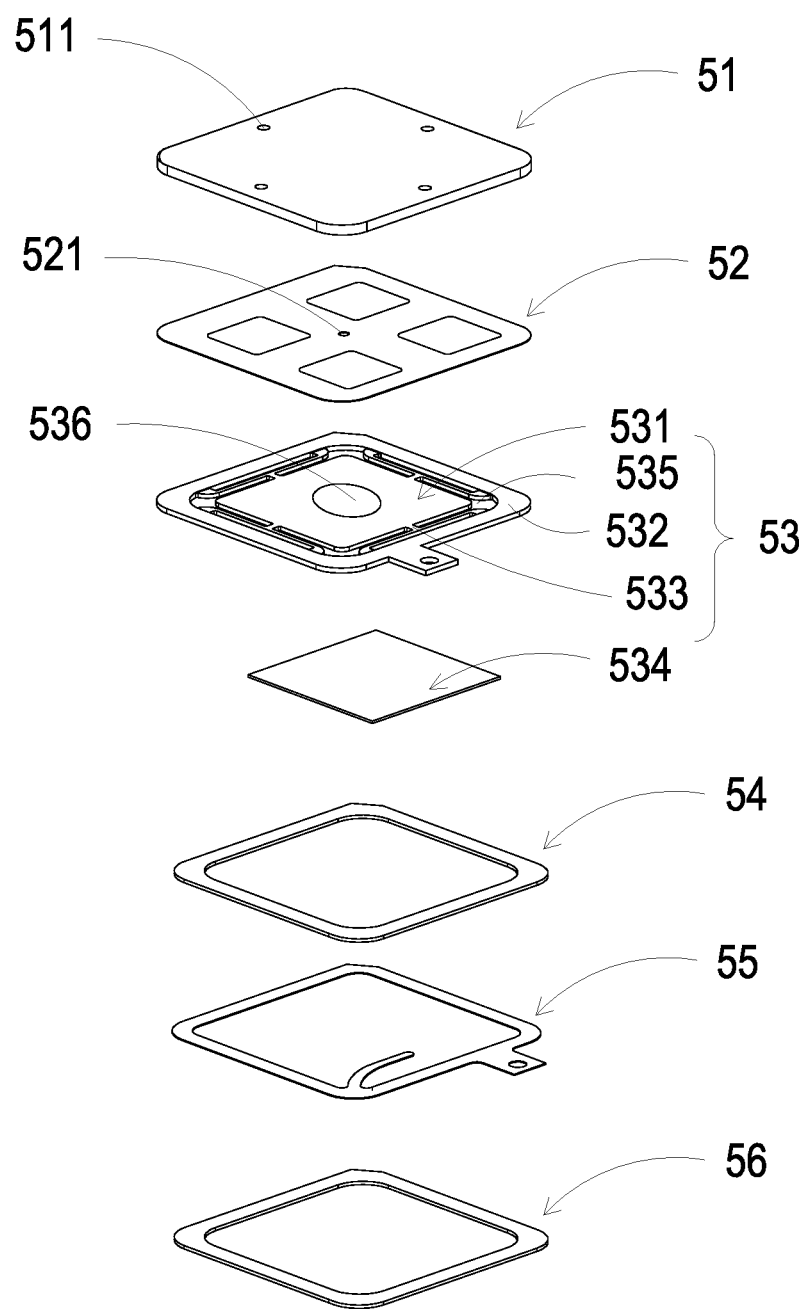
FIG. 12A is a schematic exploded view illustrating a micro pump of the wearable display device according to the embodiment of the present disclosure.
Figure 12B:
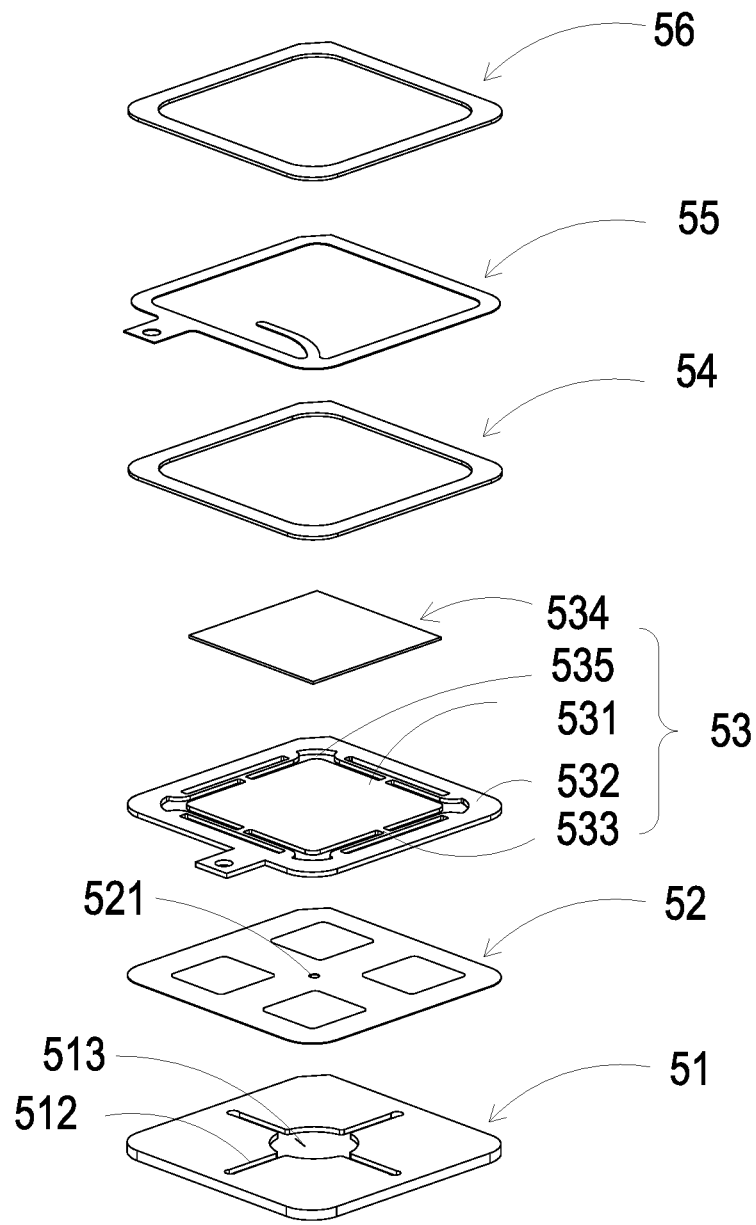
FIG. 12B is a schematic exploded view illustrating the micro pump of the wearable display device according to the embodiment of the present disclosure from another angle.
Figure 13A:
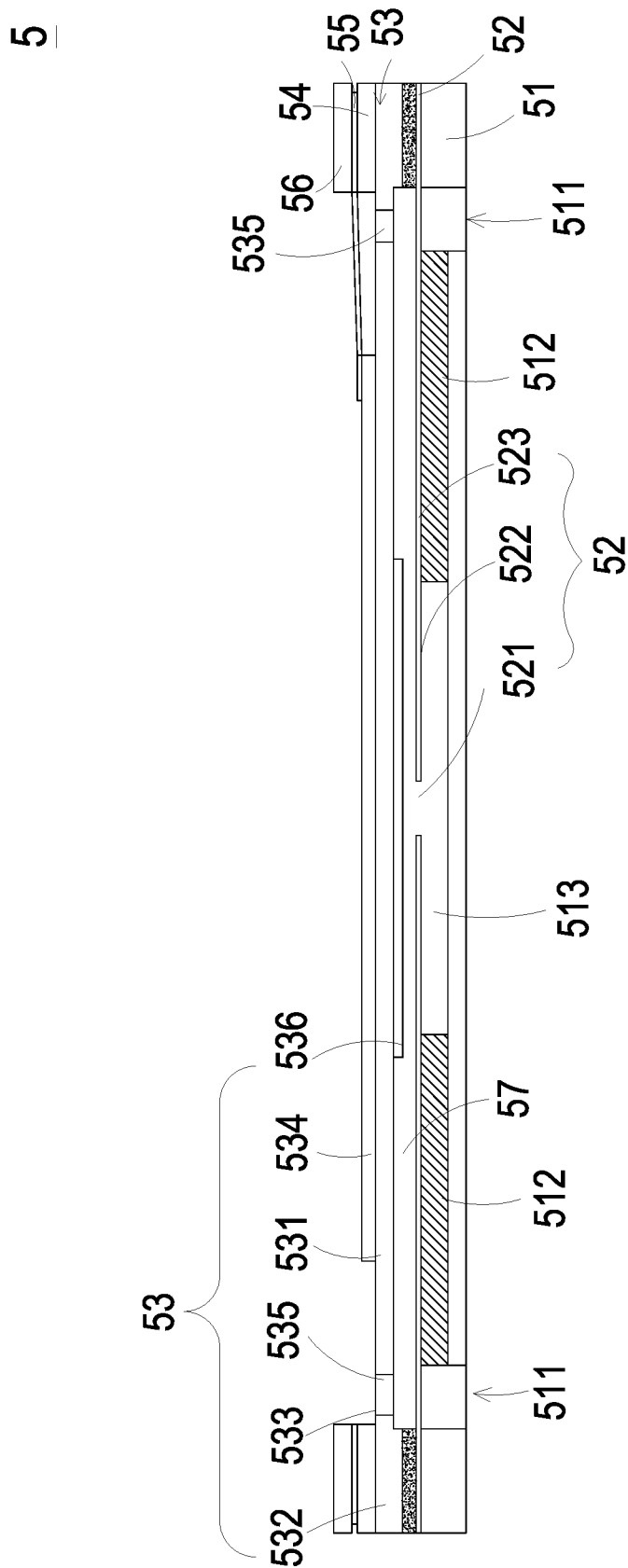
FIG. 13A is a cross sectional view illustrating the micro pump of the wearable display device according to the embodiment of the present disclosure.

Please refer to FIG. 12A, FIG. 12B and FIG. 13A. In the embodiment, the resonance plate 52 attached to the inlet plate 51 has a central aperture 521, a movable part 522 and a fixed part 523. The central aperture 521 is disposed at a center of the resonance plate 52, and is corresponding in position to the convergence chamber 513 of the inlet plate 51. The movable part 522 surrounds the central aperture 521 and is corresponding in position to the convergence chamber 513. The fixed part 523 surrounds the movable part 522 and is fixedly attached on the inlet plate 51.

Please refer to FIG. 12A, FIG. 12B and FIG. 13A again. In the embodiment, the piezoelectric actuator includes a suspension plate 531, an outer frame 532, at least one bracket 533 and a piezoelectric element 534, at least one vacant space 535 and a bulge 536. The suspension plate 531 is square-shaped because the square suspension plate 531 is more power-saving than the circular suspension plate. Generally, the consumed power of the capacitive load operated under specific resonance frequency is positively related to the resonance frequency. Since the resonance frequency of the square suspension plate 531 is obviously lower than that of the circular square suspension plate, the consumed power of the square suspension plate 531 is fewer. Therefore, the square suspension plate 531 in this embodiment is more effective in power-saving. In the embodiment, the outer frame 532 is disposed around the periphery of the suspension plate 531. The at least one bracket 533 is connected between the suspension plate 531 and the outer frame 532 for elastically supporting the suspension plate 531. The piezoelectric element 534 has a side, and a length of the side of the piezoelectric element 534 is less than or equal to that of the suspension plate 531. The piezoelectric element 534 is attached on a surface of the suspension plate 531. When a voltage is applied to the piezoelectric element 534, the suspension plate 531 is driven to undergo the bending vibration. The at least one vacant space 535 is formed between the suspension plate 531, the outer frame 532 and the at least one bracket 533 for allowing the gas to flow therethrough. The bulge 536 is formed on a surface of the suspension plate 303a, which is opposite to the surface that the piezoelectric element 534 attached on. In the embodiment, the formation of the bulge 536 may be completed by using an etching process on the suspension plate 531. Accordingly, the bulge 536 on the suspension plate 531 is integrally formed and protrudes from the surface opposite to the surface that the piezoelectric element 534 attached on, thereby formed a stepped structure.

Please refer to FIG. 12A, FIG. 12B and FIG. 13A. In the embodiment, the inlet plate 51, the resonance plate 52, the piezoelectric actuator 53, the first insulation plate 54, the conducting plate 55 and the second insulation plate 56 are stacked and assembled sequentially. A chamber space 57 is formed between the suspension plate 531 and the resonance plate 52, and the chamber space 57 can be formed by filling a gap between the resonance plate 52 and the outer frame 532 of the piezoelectric actuator 53 with a material, such as a conductive adhesive, but not limited thereto. Thus, a specific depth between the resonance plate 52 and the suspension plate 531 can be maintained to allow the gas to pass rapidly. In addition, since the resonance plate 52 and the suspension plate 531 are maintained at a suitable distance, so that the contact interference therebetween is reduced and the generated noise can be largely reduced. In some other embodiments, the thickness of the conductive adhesive filled into the gap between the resonance plate 52 and the outer frame 532 of the piezoelectric actuator 53 is reduced by increasing the height of the outer frame 532 of the piezoelectric actuator 53. Accordingly, the entire structure of the micro pump 5 would not be indirectly affected by the hot pressing temperature and the cooling temperature owing to the filling material of conductive adhesive, thereby avoiding the situation that the actual spacing of the chamber space 57 is affected by the thermal expansion and contraction of the filling material of the conductive adhesive, but are not limited thereto. Moreover, the height of the chamber space 57 also affects the transmission efficiency of the micro pump 5. Therefore, it is important to maintain a fixed height of the chamber space 57 for the purpose of achieving stable transmission efficiency of the micro pump 5.

Figure 13B:
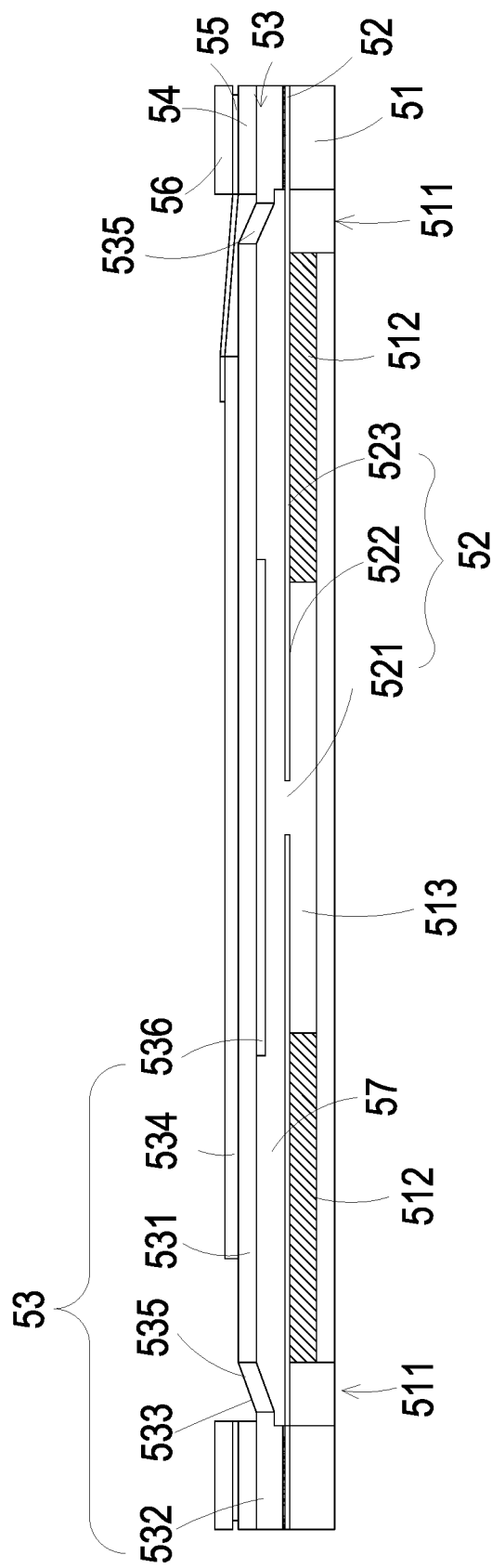
FIG. 13B is a cross sectional view illustrating the micro pump of the wearable display device according to another embodiment of the present disclosure.

Please refer to FIG. 13B. In some other embodiments of the piezoelectric actuator 53, the suspension plate 531 can be extended out with a certain distance in a direction away from the resonance plates 52 by stamping. The extended distance can be adjusted through the at least one bracket 533 formed between the suspension plate 531 and the outer frame 532, so as to make the surface of the bulge 536 disposed on the suspension plate 531 and the surface of the outer frame 532 not coplanar. The piezoelectric actuator 53 is assembled to the resonance sheet 52 by attaching the piezoelectric actuator 53 onto the fixed portion 523 of the resonance sheet 52 through hot pressing with applying a small amount of filling material (such as the conductive adhesive) on the assembly surface of the outer frame 532. In this embodiment, through the structure improvement of the chamber space 57 obtained by stamping the suspension plate 531 of the piezoelectric actuator 53 and maintaining a chamber space 57 between the surface of the suspension plate 531 and the resonance sheet 52, the required chamber space 57 can be obtained by directly adjusting the extension distance of the suspension plate 531 of the piezoelectric actuator 53. This could effectively simplify the structural design of the chamber space 57, and also simplify the manufacturing process and shortens the manufacturing time of the chamber space 57. Moreover, the first insulation sheet 54, the conductive sheet 55, and the second insulation sheet 56 are all thin sheets with a frame like structure, and are sequentially stacked and assembled on the piezoelectric actuator 53 to form the main structure of the micro pump 5.

Figure 13C:
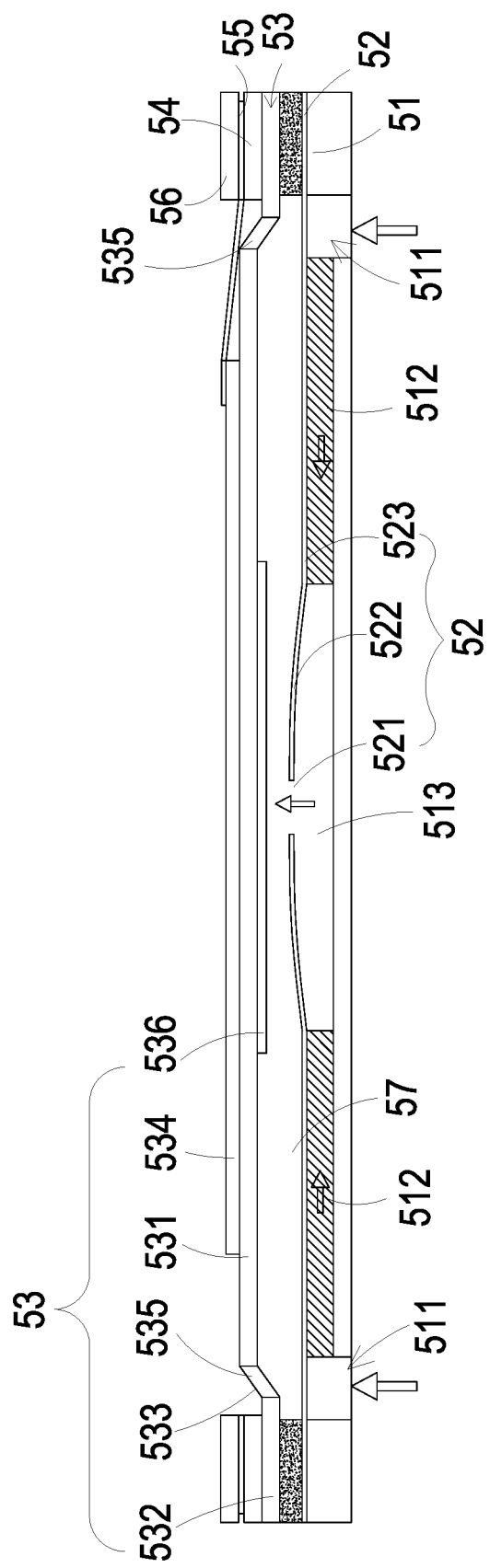
FIGS. 13C to 13E schematically illustrate the operation steps of the micro pump of the wearable display device according to the embodiment of the present disclosure.
Figure 13D:
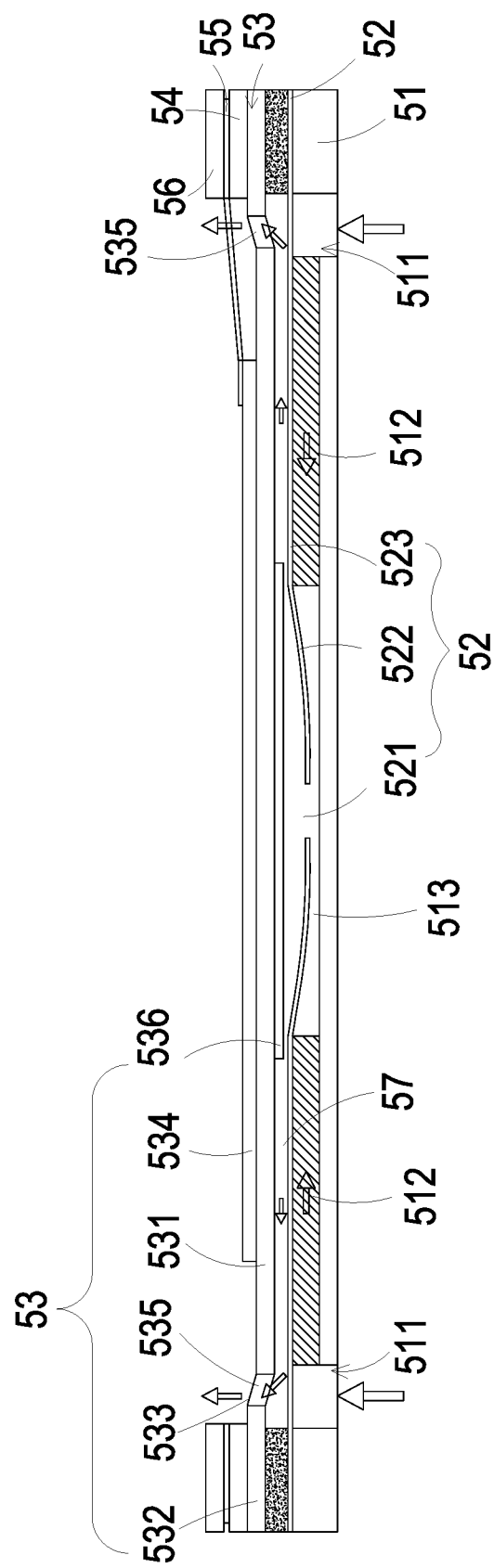
Figure 13E:
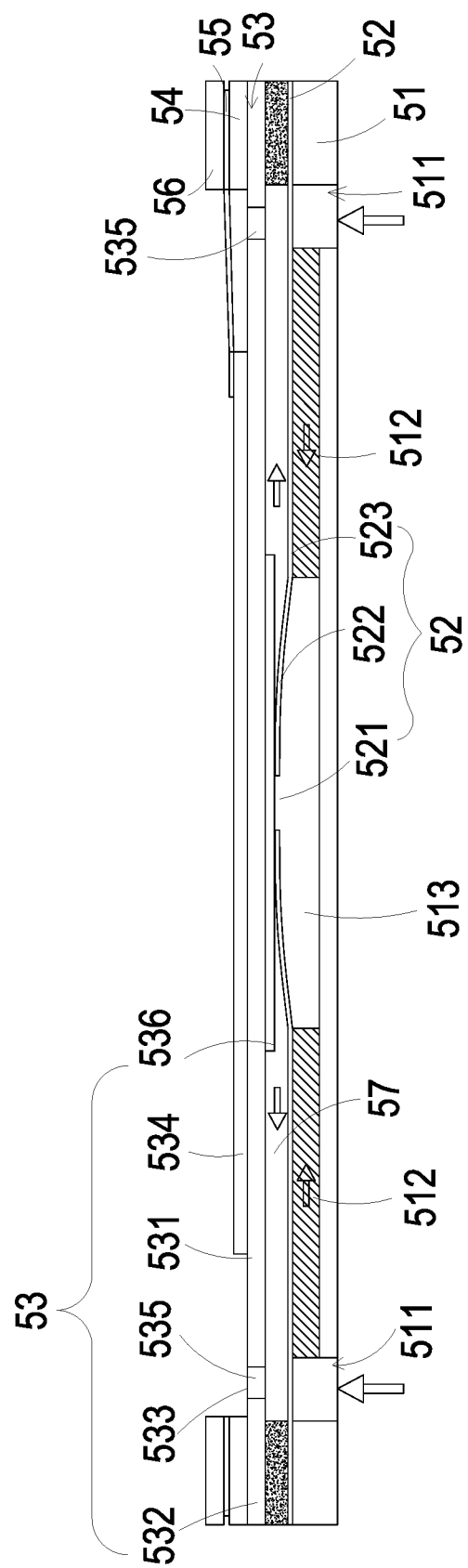
Figure 14:
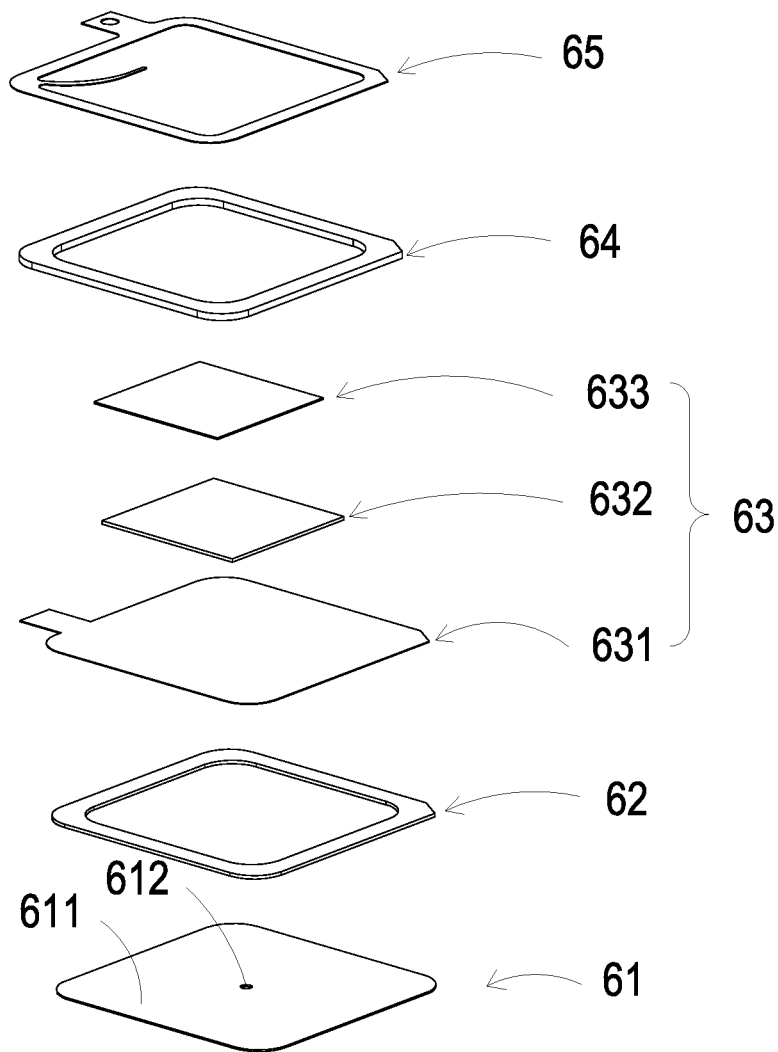
FIG. 14 is a schematic exploded view illustrating a blower-type micro pump as a second actuator of the inflatable actuation module of the present disclosure.

In order to understand the operation steps in transmitting gas of the aforementioned micro pump 5, please refer to FIG. 13C to FIG. 13E. Please refer to FIG. 13C first, the piezoelectric element 534 of the piezoelectric actuator 53 deforms after being applied with a driving voltage, and the piezoelectric element 534 drives the suspension plate 531 to move upwardly and to move away from the inlet plate 531. Thus, the volume of the chamber space 57 is increased to generate a negative pressure inside the chamber space 57, thereby drawing the gas in the convergence chamber 513a into the chamber space 57. At the same time, owing to the resonance effect, the resonance sheet 52 moves upwardly and away from the inlet plate 51, and thus increases the volume of the convergence chamber 513. Furthermore, since the gas inside the convergence chamber 513 is drawn into the chamber space 57, the convergence chamber 513 is in a negative pressure state, and the gas can be drawn into the convergence chamber 513 through the inlet hole 511 and the convergence channel 512, and then into the chamber space 57 through the central aperture 521. Then, please refer to FIG. 13D. The piezoelectric element 534 drives the suspension plate 531 to move downwardly toward the inlet plate 51, and compresses the chamber space 57. Similarly, since the movable portion 522 of the resonance sheet 52 resonates with the suspension plate 531, the resonance sheet 52 also moves downwardly and toward the inlet plate 51, thereby pushing the gas in the chamber space 57 to move upwardly to be transmitted out of the micro pump 5 through the at least one gap 535 so as to achieve gas transmission. Last, please refer to FIG. 13E. When the suspension plate 531 moves resiliently to its original position, the resonance sheet 52 still moves upwardly and away from the inlet plate 531 due to its inertia momentum. At this time, the resonance sheet 52 compresses the chamber space 57, so that the gas in the chamber space 57 is moved toward the gap 535 and the volume of the convergence chamber 513 is increased. Accordingly, the gas can be drawn into the convergence chamber 513 continuously through the inlet holes 511 and the convergence channels 512 and can be converged at the convergence chamber 513. Through continuously repeating the operation steps of the micro pump 5 shown in FIG. 13C to FIG. 13E, the micro pump 5 can make the gas continuously enter into the flow paths formed by the inlet plate 51 and the resonance sheet 52 from the inlet holes 511, thereby generating a pressure gradient. The gas is then transmitted outward through the gap 535. As a result, the gas can flow at a relatively high speed, thereby achieving the effect of gas transmission of the micro pump 5.

Please refer to FIG. 14 and FIG. 15A to FIG. 15C, a blower type micro pump 6 is illustrated. The blower type micro pump 6 includes a nozzle plate 61, a chamber frame 62, an actuation body 63, an insulation frame 64, and a conductive frame 65. The nozzle plate 61 is made of a flexible material, and the nozzle plate 61 has a suspension sheet 611 and a hollow hole 612. The suspension sheet 611b is a flexible sheet, which can bend and vibrate, but not limited thereto. The shape of the suspension sheet 611 may be one of square, circle, ellipse, triangle, and polygon. The hollow hole 612 penetrates the center portion of the suspension sheet 611 for allowing the gas to flow therethrough.

The chamber frame 62 is stacked on the nozzle plate 61, and the shape of the chamber frame 62 is corresponding to the shape of the nozzle plate 61. The actuation body 63 is stacked on the chamber frame 62, and a resonance chamber 66 is formed between the chamber frame 62, the actuation body 63, and the suspension sheet 611. The insulation frame 62 is stacked on the actuation body 63. The appearance of the insulation frame 64 is similar to the appearance of the chamber frame 62. Moreover, the actuation body 63 further includes a piezoelectric carrier plate 631, an adjusting resonance plate 632, and a piezoelectric plate 633. The piezoelectric carrier plate 631 is stacked on the chamber frame 62. The adjusting resonance plate 632 is stacked on the piezoelectric carrier plate 631. The piezoelectric plate 633 is stacked on the adjusting resonance plate 632. The adjusting resonance plate 632 and the piezoelectric plate 633 are accommodated in the insulation frame 64. The conductive frame 65 is electrically connected to the piezoelectric plate 633. The piezoelectric carrier plate 631 and the adjusting resonance plate 632 are both made of the conductive materials. The piezoelectric carrier plate 631 is electrically connected to a driving circuit (not shown) on the circuit board 15 so as to receive a driving signal (a driving frequency and a driving voltage). The piezoelectric carrier plate 631, the adjusting resonance plate 632, the piezoelectric plate 633, and the conductive frame 65 may together form a circuit for transmitting the driving signal, and the insulation frame 64 is provided for electrically isolating the conductive frame 65 from the actuation body 63 for avoiding short circuit, thereby the driving signal can be transmitted to the piezoelectric plate 633. When the piezoelectric plate 633 receives the driving signal (a driving frequency and a driving voltage), the piezoelectric plate 633 deforms owing to the piezoelectric effect, and thus the piezoelectric carrier plate 631 and the adjusting resonance plate 632 are driven to perform reciprocating vibration correspondingly.

As mentioned above, the adjusting resonance plate 632 is disposed between the piezoelectric plate 633 and the piezoelectric carrier plate 631 as a cushion element so as to adjust the vibration frequency of the piezoelectric carrier plate 631. Generally, the thickness of the adjusting resonance plate 632 is greater than the thickness of the piezoelectric carrier plate 631. The thickness of the adjusting resonance plate 632 may be changed to adjust the vibration frequency of the actuation body 63.

Figure 15A:
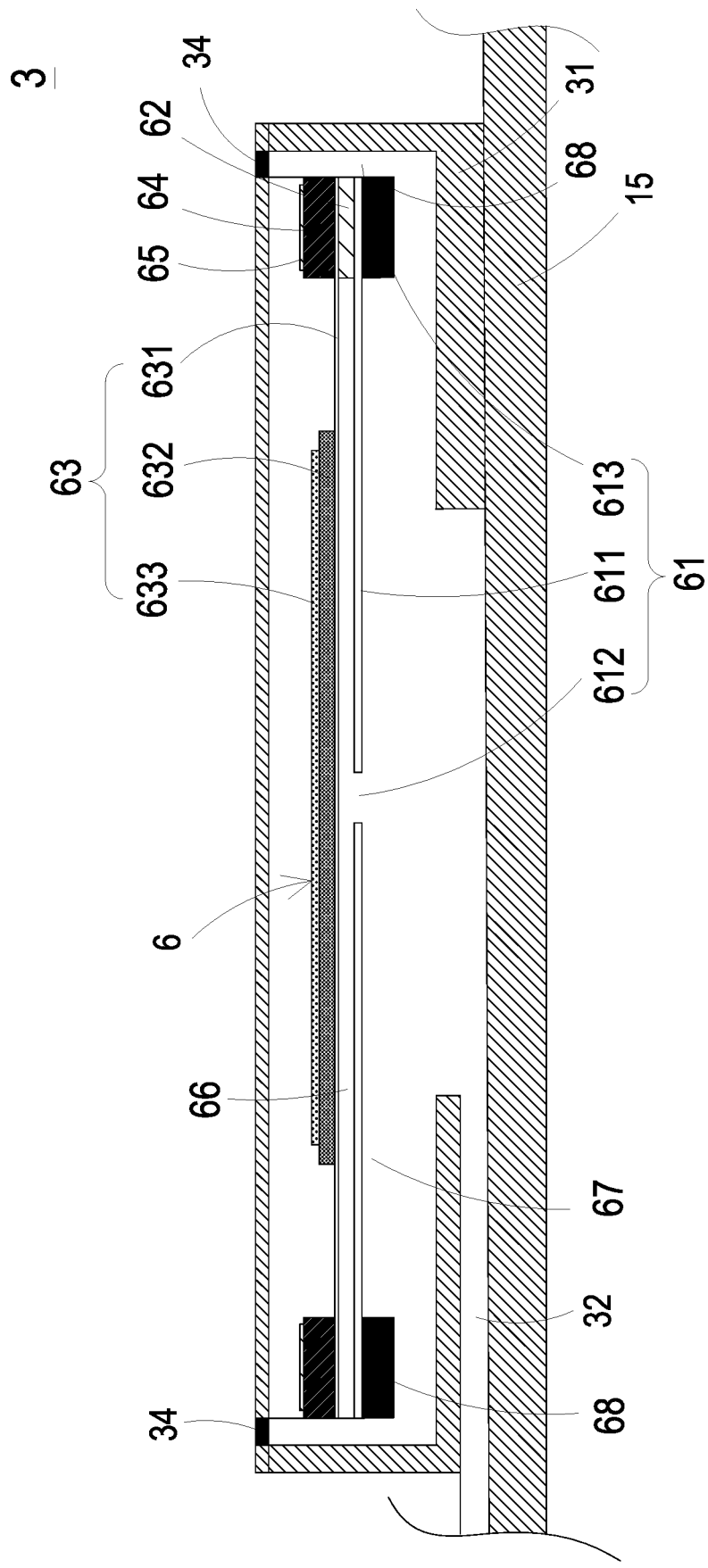
FIG. 15A is a cross sectional view illustrating the blower-type micro pump as the second actuator of the inflatable actuation module of the present disclosure.
Figure 15B:
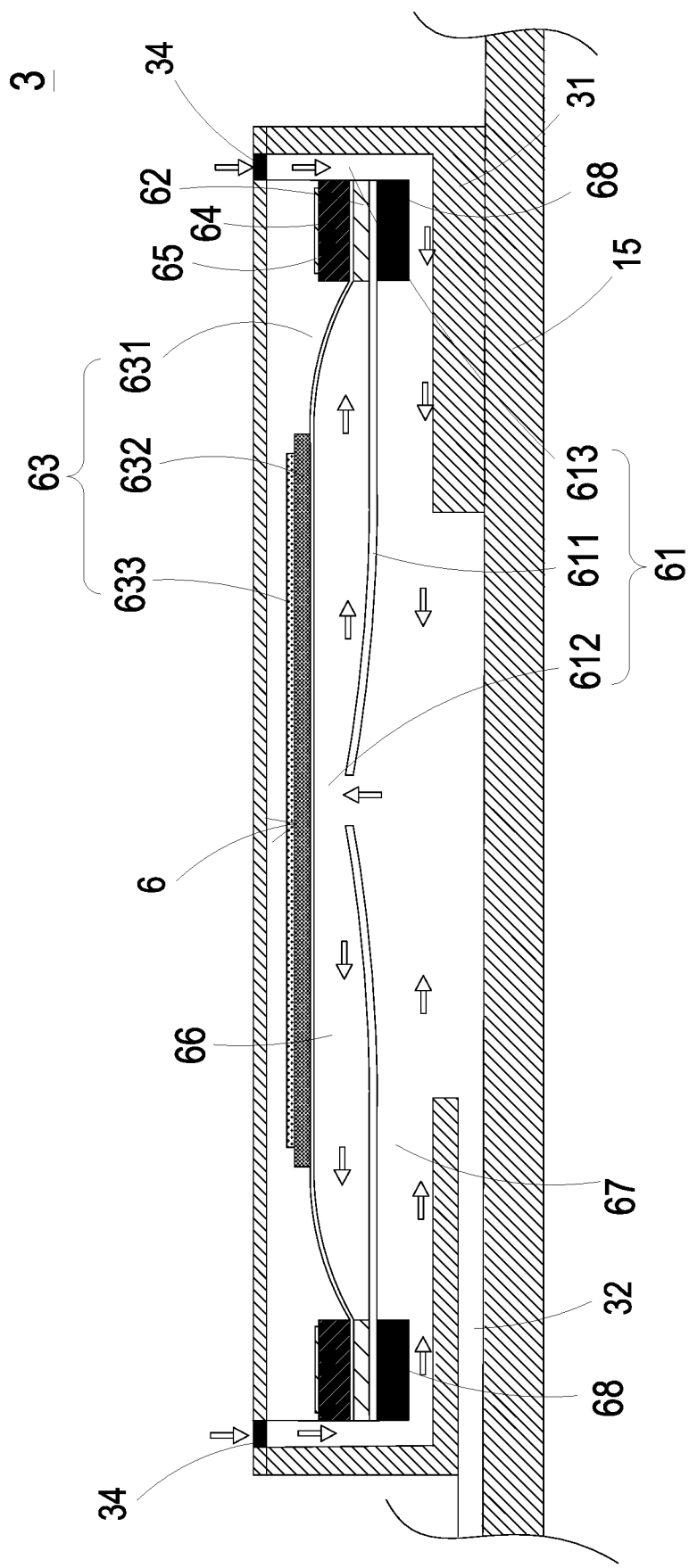
FIGS. 15B to 15C schematically illustrate the operation steps of the blower-type micro pump as the second actuator of the inflatable actuation module in FIG. 15A.
Figure 15C:
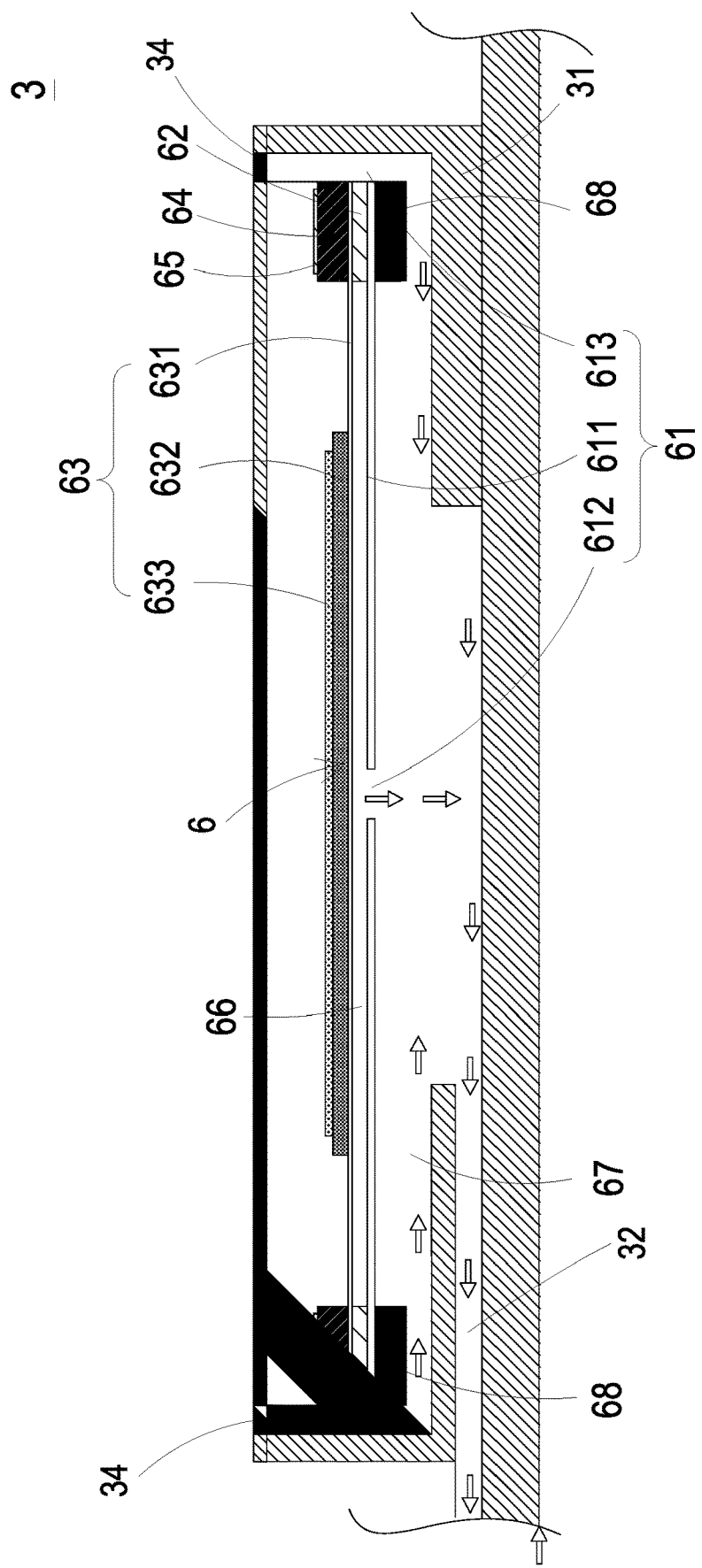

Please refer to FIG. 15A, FIG. 15B, and FIG. 15C. The nozzle plate 61, the chamber frame 62, the actuation body 63, the insulation frame 64, and the conductive frame 65 are sequentially stacked and assembled with each other. The bottom of the nozzle plate 61 is supported and positioned on a positioning bump 68, so that a surrounding gap 613 is defined between an outer portion and a bottom portion of the suspension sheet 611 of the blower type micro pump 6 for gas to pass therethrough.

Please refer to FIG. 15A first. A gas flow chamber 67 is formed between a bottom of the nozzle plate 61 and the bottom surface of the positioning bump 68. The gas flow chamber 67 is in communication with, through the hollow hole 612 of the nozzle plate 61, the resonance chamber 66 formed between the actuation body 63, the chamber frame 62, and the suspension sheet 611. Through controlling the vibration frequency of the gas in the resonance chamber 66 and making the vibration frequency of the gas in the resonance chamber 66 nearly the same with the vibration frequency of the suspension sheet 611, the resonance chamber 66 and the suspension sheet 611 can generate the Helmholtz resonance effect so as to improve the transmission efficiency of the gas.

Please refer to FIG. 15B. When the piezoelectric plate 633 moves in a direction away from the bottom surface of the positioning bump 68, the piezoelectric plate 633 drives the suspension sheet 611 of the nozzle plate 61 to move in the direction away from the bottom surface of the positioning bump 68 correspondingly. Hence, the volume of the gas flow chamber 67 expands dramatically, so that the internal pressure of the gas flow chamber 67 decreases and creates a negative pressure, thereby drawing the gas outside the blower type micro pump 6 to flow into the blower type micro pump 6 through the vacant space 613 and enter into the resonance chamber 66 through the hollow hole 612, thereby increasing the gas pressure of the resonance chamber 66 and thus generating a pressure gradient. Further, as shown in FIG. 15C, when the piezoelectric plate 633 drives the suspension sheet 611 of the nozzle plate 61 to move toward the bottom surface of the positioning bump 68, the gas inside the resonance chamber 66 is pushed to flow out quickly through the hollow hole 612 so as to further push the gas inside the gas flow chamber 67, thereby the converged gas can be quickly and massively ejected out of the bottom surface of the positioning bump 68 in a state closing to an ideal gas state under the Benulli's law. Therefore, through repeating the steps as shown in FIG. 15B and FIG. 15C, the piezoelectric plate 633 can bend and vibrate reciprocatingly. Further, after the gas is discharged out of the resonance chamber 66, the internal pressure of the resonance chamber 66 is lower than the equilibrium pressure due to the inertia, as a result, the pressure difference guides the gas outside the resonance chamber 66 into the resonance chamber 66 again. Thus, through controlling the vibration frequency of the gas inside the resonance chamber 66 to be close the vibration frequency of the piezoelectric plate 633 and generate the Helmholtz resonance effect, high-speed and large-volume gas transmission can be achieved.

Please refer to FIG. 17A, FIG. 17B and FIG. 18A to FIG. 18C, a microelectromechanical systems (MEMS) micro pump 7 is illustrated. The MEMS micro pump 7 manufactured through surface micromachining techniques has a reduced size and volume. The MEMS micro pump 7 includes a substrate 71, an oxide layer 72, a vibration layer 73, and a piezoelectric component 74. The substrate 71 is a silicon substrate and formed with at least one inlet 711 by etching.

The oxide layer 72 formed and stacked on the substrate 71 by deposition is formed with a plurality of convergence channels 721 and a convergence chamber 722 by etching. The convergence channels 721 are in communication between the at least one inlet 711 of the substrate 71 and the convergence chamber 722. The deposition process may be a physical vapor deposition (PVD) process, a chemical vapor deposition (CVD) process, or a combination thereof, but not limited thereto. The detailed descriptions about the deposition process are omitted.

The vibration layer 73 is formed and stacked on the oxide layer 72 by deposition. The vibration layer 73 includes a silicon wafer layer 731, a second oxide layer 732, and a metal layer 733. The metal layer 733 formed and stacked on the oxide layer 72 by deposition is formed with a through hole 7331, a vibration portion 7332, and a fixed portion 7333 by etching. The etching process may be a wet etching process, a dry etching process, or a combination thereof, but not limited thereto. The detailed descriptions about the etching process are omitted.

The through hole 7331 is formed at a center portion of the metal layer 733 by etching. The vibration portion 7332 is formed on a periphery of the through hole 7331. The fixed portion 7333 is formed on a periphery of the metal layer 733.

The second oxide layer 732 is formed and stacked on the metal layer 733 by deposition, and the second oxide layer 732 is formed with an oxide layer hole 7321 by etching.

The silicon wafer layer 731 formed and stacked on the second oxide layer 732 by deposition is formed with an actuation portion 7311, an outer peripheral portion 7312, a plurality of connection portions 7313, and a plurality of fluid channels 7314 by etching. The actuation portion 7311 is formed at a center portion of the silicon wafer layer 731. The outer peripheral portion 7312 is formed around a periphery of the actuation portion 7311. The connection portions 7313 are respectively connected between the actuation portion 7311 and the outer peripheral portion 7312. The fluid channels 7314 are respectively formed between the actuation portion 7311 and the outer peripheral portion 7312 and between the connection portions 7313. Accordingly, a compression chamber is formed by the silicon wafer layer 731 and the oxide layer hole 7321 of the second oxide layer 732.

The piezoelectric component 74 formed and stacked on the actuation portion 7311 of the silicon wafer layer 731 by deposition includes a lower electrode layer 741, a piezoelectric layer 742, an insulation layer 743, and an upper electrode layer 744. The lower electrode layer 741 is stacked and formed on the actuation portion 7311 of the silicon wafer layer 731 by deposition, and the piezoelectric layer 742 is stacked and formed on the lower electrode layer 741. The insulation layer 743 is formed and stacked on a portion of a surface of the piezoelectric layer 742 and on a portion of a surface of the lower electrode layer 741 by deposition, and the upper electrode layer 744 is stacked on the insulation layer 743 and the remaining portion of the surface of the piezoelectric layer 742 which is not covered by the insulation layer 743, and the upper electrode layer 744 is provided for electrically connected to the piezoelectric layer 742.

Figure 18A:
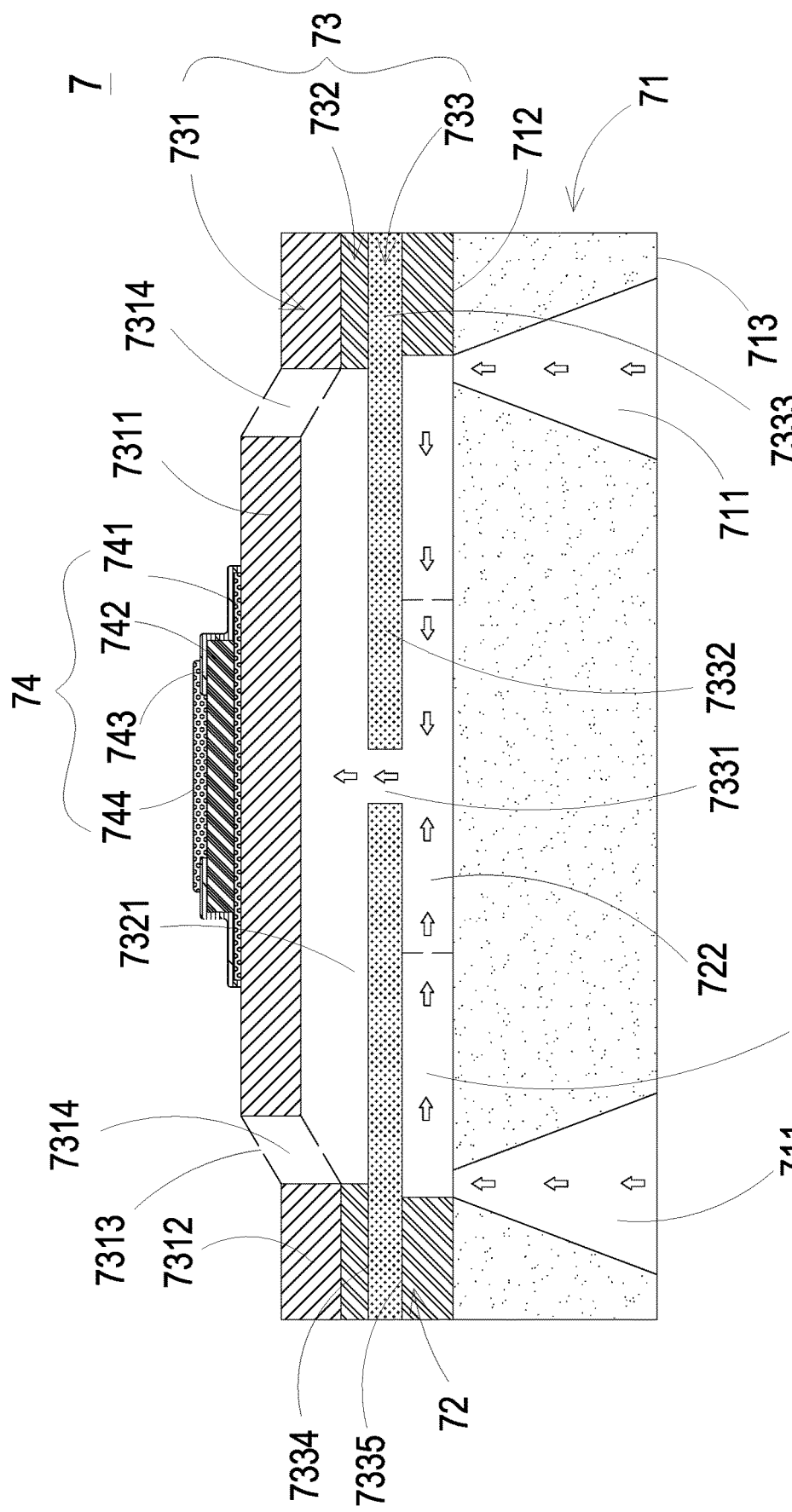
FIGS. 18A to 18C schematically illustrate the operation steps of the microelectromechanical-system micro pump of the wearable display device according to the embodiment of the present disclosure.
Figure 18B:
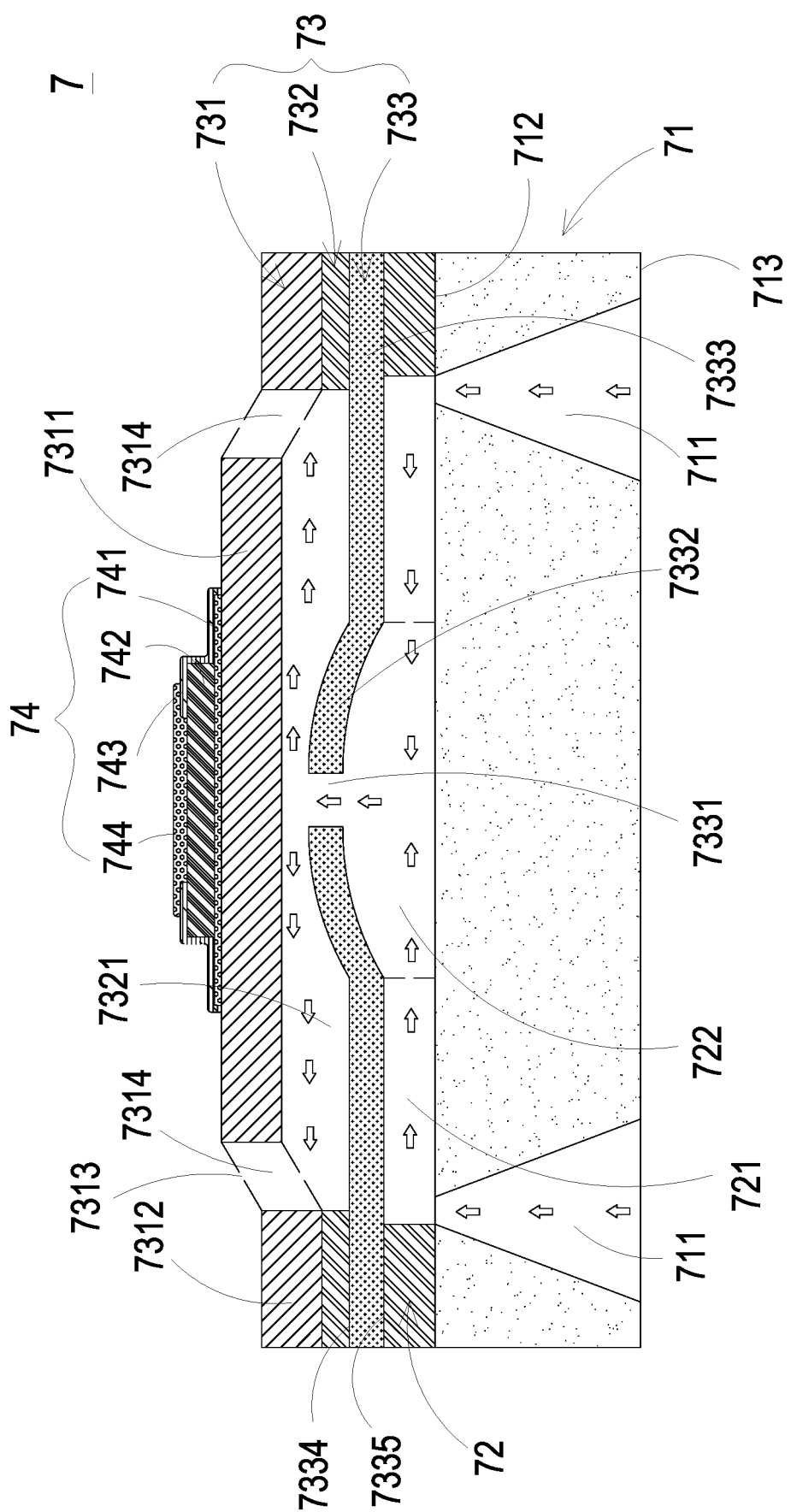
Figure 18C:
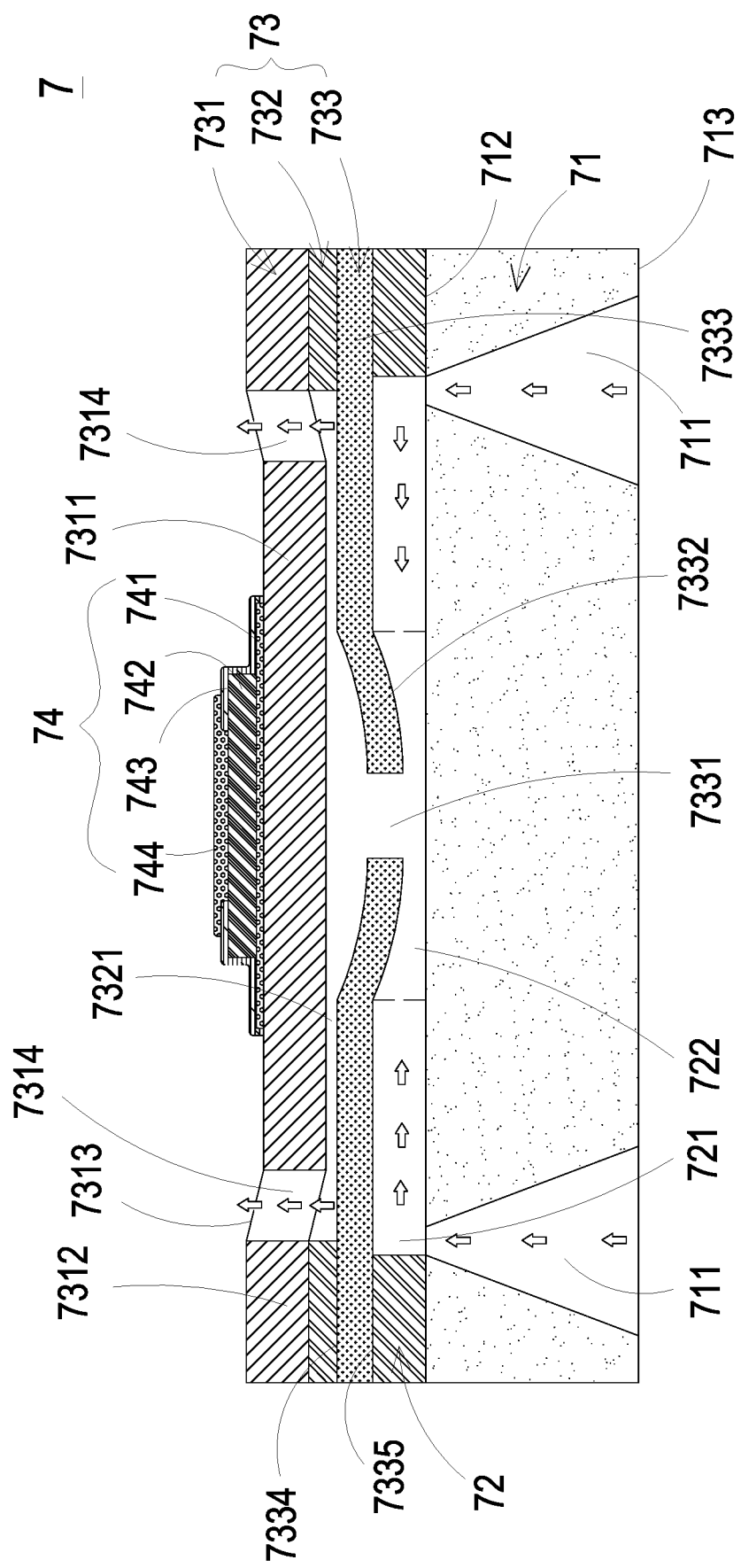

As for how the MEMS micro pump 7 performs the gas transmission, please refer to FIG. 18A. When the lower electrode layer 741 and the upper electrode layer 744 of the piezoelectric component 74 receive a driving signal (not shown in the figure), the piezoelectric layer 742 starts to deform because of the reverse piezoelectric effect, thereby driving the actuation portion 7311 of the silicon wafer layer 731 to move correspondingly. When the actuation portion 7311 is driven by the piezoelectric component 74 away from the second oxide layer 732 and thus the distance between the actuation portion 7311 and the second oxide layer 732 increases, the volume of the compression chamber increases as well, and a negative pressure is created in the compression chamber as a result, and thus the gas outside the substrate 71 is drawn into the compression chamber through the inlet 711, and further enters into the convergence channels 721 and the convergence chamber 722 of the oxide layer 72. Please refer to FIG. 18B, when the actuation portion 7311 is driven by the piezoelectric component 74, the vibration portion 7332 of the metal layer 733 is moved due to the resonance effect. When the vibration portion 7332 is moved, the space of the compression chamber is compressed and the gas in the compression chamber is pushed to the fluid channels 7314 of the silicon wafer layer 731. Please refer to FIG. 18C. When the piezoelectric component 74 drives the actuation portion 7311 of the silicon wafer layer 731 to move in an opposite direction, the vibration portion 7332 of the metal layer 733 is also driven and moved by the actuation portion 7311, so that the gas can be transmitted through the fluid channels 7314 and thus forces the gas in convergence chamber 722 to enter into the compression chamber through the through hole 7331 at the same time. Hence, when the actuation portion 7331 is driven by the piezoelectric component 74 again later, the volume of the compression chamber dramatically increases, thereby generating a larger suction force to draw the gas into the compression chamber. Through repeating the aforementioned steps mentioned in FIG. 18A to FIG. 18C, the actuation portion 7311 can be continually driven by the piezoelectric component 74 to move reciprocatingly, and the vibration portion 7332 is also driven to move reciprocatingly correspondingly. Thus, the internal pressure of the compression chamber of the MEMS micro pump 7 can be changed periodically so as to draw and discharge the gas continually, thereby completing the pumping process of the MEMS micro pump 7.

Based on the above descriptions, the first actuator 21, the second actuator 33, and the third actuators 4 may be a micro pump, a blower type micro pump, or a MEMS micro pump. An embodiment in which the blower type micro pump 6 is applied to the inflation actuation module 3 is further described in the following paragraphs. As shown in FIG. 2A and FIG. 2B, in this embodiment, the second actuator is a blower type micro pump. Please further refer to FIG. 15A, FIG. 15B, and FIG. 15C. The nozzle plate 61, the chamber frame 62, the actuation body 63, the insulation frame 64, and the conductive frame 65 of the blower type micro pump 6 are sequentially stacked and assembled with each other and the blower type micro pump 6 is disposed and positioned in the base member 31, so that the bottom of the nozzle plate 61 is supported and positioned on the positioning bump 68. Therefore, a surrounding gap 613 is defined between the inner edge of the suspension sheet 611 of the blower type micro pump 6 and the inner edge of the base member 31 for gas to pass therethrough. The valve component 34 is corresponding to the vacant space 613 and covers the whole base member 31 so as to control the gas introduction of the blower type micro pump 6.

Please refer to FIG. 15A first. A gas flow chamber 67 is formed between a bottom of the nozzle plate 61 and the bottom surface of the base member 31. The gas flow chamber 67 is in communication with, through the hollow hole 612 of the nozzle plate 61, the resonance chamber 66 formed between the actuation body 63, the chamber frame 62, and the suspension sheet 611. Through controlling the vibration frequency of the gas in the resonance chamber 66 and making the vibration frequency of the gas in the resonance chamber 66 nearly the same with the vibration frequency of the suspension sheet 611, the resonance chamber 66 and the suspension sheet 611 can generate the Helmholtz resonance effect so as to improve the transmission efficiency of the gas.

Please refer to FIG. 15B. When the piezoelectric plate 633 moves in a direction away from the bottom surface of the base member 31, the piezoelectric plate 633 drives the suspension sheet 611 of the nozzle plate 61 to move in the direction away from the bottom surface of the base member 31 correspondingly. Hence, the volume of the gas flow chamber 67 expands dramatically, so that the internal pressure of the gas flow chamber 67 decreases and creates a negative pressure, thereby drawing the gas outside the blower type micro pump 6 to flow into the blower type micro pump 6 through the vacant space 613 and enter into the resonance chamber 66 through the hollow hole 612, thereby increasing the gas pressure of the resonance chamber 66 and thus generating a pressure gradient. Further, as shown in FIG. 15C, when the piezoelectric plate 633 drives the suspension sheet 611 of the nozzle plate 61 to move toward the bottom surface of the base member 31, the gas inside the resonance chamber 66 is pushed to flow out quickly through the hollow hole 612 so as to further push the gas inside the gas flow chamber 67, thereby the converged gas can be quickly and massively ejected out of the bottom surface of the base member 31 and into the ventilation channel 32 in a state closing to an ideal gas state under the Benulli's law. Therefore, through repeating the steps as shown in FIG. 15B and FIG. 15C, the piezoelectric plate 633 can bend and vibrate reciprocatingly. Further, after the gas is discharged out of the resonance chamber 66, the internal pressure of the resonance chamber 66 is lower than the equilibrium pressure due to the inertia, as a result, the pressure difference guides the gas outside the resonance chamber 66 into the resonance chamber 66 again. Thus, through controlling the vibration frequency of the gas inside the resonance chamber 66 to be close the vibration frequency of the piezoelectric plate 633 and generate the Helmholtz resonance effect, high-speed and large-volume gas transmission can be achieved.

As mentioned above, as shown in FIG. 2B, the valve component 34 covers the second actuator 33. Moreover, please refer to FIG. 15A to FIG. 15C. The valve component 34 is corresponding to the vacant space 613 of the blower type micro pump 6. When the blower type micro pump 6 and the valve component 34 are driven, the valve component 34 is opened to control the gas introduction of the blower type micro pump 6, and the blower type micro pump 6 is actuated to transmit the gas to the ventilation channel 32 for gas collection, and the blower type micro pump 6 further transmits the gas to the inflatable airbag 13 for inflating the inflatable airbag 13 at the wearing surface of the main body 1, so as to allow the main body 1 to be stably positioned on and fitted with the head of a user.

Accordingly, in the wearable display device according to one or some embodiments of the present disclosure, the heat dissipation processing module construed by the first actuator of the micro pump and cooling chip can perform heat dissipation effectively for the micro-processing chip inside the wearable display device so as to improve the operation efficiency of the micro-processing chip. Hence, the entire device may be miniaturized and can perform the heat dissipation function quietly. Moreover, the second actuator of the micro pump is provided for inflating the fillable airbag, so that the wearable display device can provide wearing comfortableness even when the wearable display device is worn by the user for a long time. Furthermore, the third actuator of the micro pump and the intraocular pressure sensor are provided for detecting the intraocular pressure of the user, so as to provide a notification to prevent the user from feeling dizzy or from having excessive intraocular pressure and cause damages for the user or affect the health for the user.

While the disclosure has been described in terms of the most practical and preferred embodiments, it is to be understood that the disclosure needs not be limited to the disclosed embodiments. On the contrary, it is intended to cover various modifications and similar arrangements included within the spirit and scope of the appended claims so as to encompass all such modifications and similar structures.

What is claimed is:

1. A wearable display device comprising:
a main body comprising a front cover, a lateral cover, an inflatable airbag, a circuit board and a microprocessor, wherein the lateral cover is connected to one side of the front cover, the inflatable airbag is attached to and positioned at one side of the lateral cover, the circuit board is positioned inside the lateral cover, and the microprocessor is packaged on the circuit board;
a heat dissipation processing module comprising a first actuator, a heat pipe and at least one cooling chip, wherein the heat pipe is contacted with a heat-generating surface of the microprocessor, the heat pipe is configured to receive a heat dissipation liquid, the first actuator and the at least one cooling chip are connected to the heat pipe and perform heat exchange on the heat pipe; and
an inflatable actuation module disposed on the circuit board and comprising a base, a ventilation channel, a second actuator and a valve component, wherein the base is positioned at the circuit board and in fluid communication with the ventilation channel, the second actuator is positioned in the base, the ventilation channel is in fluid communication with the inflatable airbag, and the valve component covers the second actuator and is capable of being opened or closed;
wherein when the second actuator and the valve component are driven, the valve component is opened, and the second actuator is enabled at the same time, whereby gas is transported through the ventilation channel to inflate the inflatable airbag.

2. The wearable display device according to claim 1, wherein the at least one cooling chip comprises a cooling surface and a heating surface, the cooling surface is disposed opposite to the heating surface, and the cooling surface is connected to the heat pipe.

3. The wearable display device according to claim 1, wherein the heat dissipation processing module includes a liquid pump, and the liquid pump is in fluid communication with an interior space of the heat pipe, whereby the heat dissipation liquid inside the heat pipe is pumped and circulated.

4. The wearable display device according to claim 1, wherein the heat dissipation processing module comprises a positioning accommodation seat, the positioning accommodation seat is disposed on the circuit board, and the positioning accommodation comprises a vent hole, wherein the first actuator is disposed in and positioned at the positioning accommodation seat and in fluid communication with the vent hole to exchange heat with the microprocessor.

5. The wearable display device according to claim 1, wherein the heat dissipation processing module comprises a positioning accommodation seat, the positioning accommodation seat is disposed on the heat pipe, and the positioning accommodation comprises a vent hole, wherein the first actuator is disposed in and positioned at the positioning accommodation seat and in fluid communication with the vent hole to exchange heat with the heat pipe.

6. The wearable display device according to claim 1, wherein the main body further comprises a communicator, and the communicator is packaged on the circuit board, wherein the communicator provide a wireless two-way data transmission through Bluetooth or Wi-Fi.

7. The wearable display device according to claim 1, wherein the main body comprises:
at least one display disposed in the lateral cover for displaying an image processed by the microprocessor;
at least one intraocular pressure sensor disposed at a center point of the at least one display and electrically connected to the circuit board for emitting an infrared light and detecting a light energy reflected from the infrared light; and
at least one third actuator disposed under the at least one display and electrically connected to the circuit board for generating a pulsed gas;
wherein when the at least one third actuator is driven to generate the pulsed gas, the at least one intraocular pressure sensor emits the infrared light and calculates the light energy of the reflected infrared light to detect an intraocular pressure data of a wearer, so that the wearable display device is allowed to display the intraocular pressure data and issue a notification message.

8. The wearable display device according to claim 1, wherein the first actuator and the second actuator are a micro pump, respectively.

9. The wearable display device according to claim 8, wherein the micro pump comprises:
an inlet plate having at least one inlet aperture, at least one convergence channel and a convergence chamber, wherein the at least one inlet aperture is disposed to inhale the gas, and the at least one convergence channel is disposed corresponding in position to the inlet aperture to guide the gas inhaled from the inlet aperture to the convergence chamber;
a resonance plate combined on the inlet plate and having a central aperture, a movable part and a fixed part, wherein the central aperture is disposed at a center of the resonance plate and is corresponding in position to the convergence chamber of the inlet plate, the movable part surrounds the central aperture and is corresponding in position to the convergence chamber, and the fixed part surrounds the movable part and is fixedly attached on the inlet plate; and
a piezoelectric actuator combined on the resonance plate and is corresponding in position to the resonance plate;
wherein a chamber space is formed between the resonance plate and the piezoelectric actuator, wherein when the piezoelectric actuator is driven, the gas introduced from the at least one inlet aperture of the inlet plate is converged to the convergence chamber through the at least one convergence channel, and flows through the central aperture of the resonance plate, whereby a resonance is generated by the piezoelectric actuator and the movable part of the resonance plate to transport and output the gas.

10. The wearable display device according to claim 7, wherein the at least one third actuator is a micro pump.

11. The wearable display device according to claim 10, wherein the micro pump comprises:
an inlet plate having at least one inlet aperture, at least one convergence channel and a convergence chamber, wherein the at least one inlet aperture is disposed to inhale the gas, and the at least one convergence channel is disposed corresponding in position to the inlet aperture to guide the gas inhaled from the inlet aperture to the convergence chamber;

a resonance plate combined on the inlet plate and having a central aperture, a movable part and a fixed part, wherein the central aperture is disposed at a center of the resonance plate and is corresponding in position to the convergence chamber of the inlet plate, the movable part surrounds the central aperture and is corresponding in position to the convergence chamber, and the fixed part surrounds the movable part and is fixedly attached on the inlet plate; and a piezoelectric actuator combined on the resonance plate and is corresponding in position to the resonance plate;

wherein a chamber space is formed between the resonance plate and the piezoelectric actuator, wherein when the piezoelectric actuator is driven, the gas introduced from the at least one inlet aperture of the inlet plate is converged to the convergence chamber through the at least one convergence channel, and flows through the central aperture of the resonance plate, whereby a resonance is generated by the piezoelectric actuator and the movable part of the resonance plate to transport and output the gas.

12. The wearable display device according to claim 1, wherein the first actuator and the second actuator are a blower-type micro pump, respectively.

13. The wearable display device according to claim 12, wherein the blower-type micro pump comprises:

a gas-injection plate comprising a suspension plate and a hollow aperture, wherein the suspension plate is permitted to undergo a bending deformation, and the hollow aperture is formed at a center of the suspension plate;

a chamber frame carried and stacked on the suspension plate;

an actuator element comprising a piezoelectric carrying plate, an adjusting resonance plate and a piezoelectric plate, wherein the piezoelectric carrying plate is carried and stacked on the chamber frame, the adjusting resonance plate is carried and stacked on the piezoelectric carrying plate, and the piezoelectric plate is carried and stacked on the adjusting resonance plate, wherein the piezoelectric plate is driven by a voltage to drive the piezoelectric carrying plate and the adjusting resonance plate and generate the bending deformation in the reciprocating manner;

an insulation frame carried and stacked on the actuator element; and a conductive frame carried and stacked on the insulation frame;

wherein the gas-injection plate is fixed for supporting and positioning, so that a vacant space is defined outside the gas-injection plate and a flowing chamber is defined at a bottom thereof for gas to flowing therethrough, and a resonance chamber is formed between the actuator element, the chamber frame and the suspension plate, wherein when the actuator element is enabled to drive the gas-injection plate to move in resonance, the suspension plate of the gas-injection plate is driven to generate the bending deformation in a reciprocating manner, and the gas is inhaled through the vacant space, flows into the flowing chamber, and is discharged out, so as to achieve gas transportation.

14. The wearable display device according to claim 7, wherein the at least one third actuator is a blower-type micro pump.

15. The wearable display device according to claim 14, wherein the blower-type micro pump comprises:

a gas-injection plate comprising a suspension plate and a hollow aperture, wherein the suspension plate is permitted to undergo a bending deformation, and the hollow aperture is formed at a center of the suspension plate;

a chamber frame carried and stacked on the suspension plate;

an actuator element comprising a piezoelectric carrying plate, an adjusting resonance plate and a piezoelectric plate, wherein the piezoelectric carrying plate is carried and stacked on the chamber frame, the adjusting resonance plate is carried and stacked on the piezoelectric carrying plate, and the piezoelectric plate is carried and stacked on the adjusting resonance plate, wherein the piezoelectric plate is driven by a voltage to drive the piezoelectric carrying plate and the adjusting resonance plate and generate the bending deformation in the reciprocating manner;

an insulation frame carried and stacked on the actuator element; and a conductive frame carried and stacked on the insulation frame;

wherein the gas-injection plate is fixed for supporting and positioning, so that a vacant space is defined outside the gas-injection plate and a flowing chamber is defined at a bottom thereof for gas to flowing therethrough, and a resonance chamber is formed between the actuator element, the chamber frame and the suspension plate, wherein when the actuator element is enabled to drive the gas-injection plate to move in resonance, the suspension plate of the gas-injection plate is driven to generate the bending deformation in a reciprocating manner, and the gas is inhaled through the vacant space, flows into the flowing chamber, and is discharged out, so as to achieve gas transportation.

16. The wearable display device according to claim 1, wherein the first actuator and the second actuator are a microelectromechanical-system micro pump, respectively.

17. The wearable display device according to claim 16, wherein the microelectromechanical-system micro pump comprises:

a substrate comprising at least one inlet aperture formed by an etching process;

an oxidation layer formed and stacked on the substrate by a deposition process, wherein the oxidation layer comprises a plurality of convergence channels and a convergence chamber formed by an etching process, and the plurality of convergence channels are in fluid communication between the convergence chamber and the at least one inlet aperture of the substrate;

a vibration layer formed and stacked on the oxidation layer by a deposition process, and comprising:
a metal layer formed and stacked on the oxidation layer by a deposition process and comprising a through hole, a vibration portion and a fixed portion formed by an etching process, wherein the through hole is formed at a center of the metal layer, the vibration portion is disposed around a peripheral region of the through hole, and the fixed portion is disposed around a peripheral region of the metal layer;

a second oxidation layer formed and stacked on the metal layer by a deposition process, and comprising a hollow aperture formed by an etching process; and a silicon chip layer formed and stacked on the second oxidation layer by a deposition process and comprising an actuating portion, an outer peripheral portion, a plurality of connecting portions and a plurality of fluid channels formed by an etching process, wherein the actuating portion is disposed at a central part of the silicon chip layer, the outer peripheral portion is disposed around an outer periphery of the actuating portion, the plurality of connecting portions are connected between the actuating portion and the outer peripheral portion, respectively, and each of the plurality of fluid channels is disposed between the actuating portion and the outer peripheral portion and located between the plurality of connecting portions, wherein a compression chamber is collaboratively defined by the silicon chip layer and the hollow aperture of the second oxidation layer; and a piezoelectric component formed and stacked on the actuating portion of the silicon chip layer by a deposition process and comprising a lower electrode layer, a piezoelectric layer, an insulation layer and an upper electrode layer, wherein the piezoelectric layer is formed and stacked on the lower electrode layer by a deposition process, the insulation layer is formed and stacked on a partial surface of the piezoelectric layer and a partial surface of the lower electrode layer by a deposition process, and the upper electrode layer is formed and stacked on the insulation layer and a remaining surface of the piezoelectric layer without the insulation layer disposed thereon by a deposition process, so as to electrically connect with the piezoelectric layer;

wherein when the piezoelectric component is driven, the gas introduced from the at least one inlet aperture of the substrate is converged to the convergence chamber through the plurality of convergence channels, and flows through the through hole of the vibration layer, whereby a resonance effect is generated by the piezoelectric component and the actuating portion of the vibration layer to transport the gas and output.

18. The wearable display device according to claim 7, wherein the at least one third actuator is a microelectromechanical-system micro pump.

19. The wearable display device according to claim 18, wherein the microelectromechanical-system micro pump comprises:
a substrate comprising at least one inlet aperture formed by an etching process;
an oxidation layer formed and stacked on the substrate by a deposition process, wherein the oxidation layer comprises a plurality of convergence channels and a convergence chamber formed by an etching process, and the plurality of convergence channels are in fluid communication between the convergence chamber and the at least one inlet aperture of the substrate;
a vibration layer formed and stacked on the oxidation layer by a deposition process, and comprising:
a metal layer formed and stacked on the oxidation layer by a deposition process and comprising a through hole, a vibration portion and a fixed portion formed by an etching process, wherein the through hole is formed at a center of the metal layer, the vibration portion is disposed around a peripheral region of the through hole, and the fixed portion is disposed around a peripheral region of the metal layer;
a second oxidation layer formed and stacked on the metal layer by a deposition process, and comprising a hollow aperture formed by an etching process; and
a silicon chip layer formed and stacked on the second oxidation layer by a deposition process and comprising an actuating portion, an outer peripheral portion, a plurality of connecting portions and a plurality of fluid channels formed by an etching process, wherein the actuating portion is disposed at a central part of the silicon chip layer, the outer peripheral portion is disposed around an outer periphery of the actuating portion, the plurality of connecting portions are connected between the actuating portion and the outer peripheral portion, respectively, and each of the plurality of fluid channels is disposed between the actuating portion and the outer peripheral portion and located between the plurality of connecting portions, wherein a compression chamber is collaboratively defined by the silicon chip layer and the hollow aperture of the second oxidation layer; and a piezoelectric component formed and stacked on the actuating portion of the silicon chip layer by a deposition process and comprising a lower electrode layer, a piezoelectric layer, an insulation layer and an upper electrode layer, wherein the piezoelectric layer is formed and stacked on the lower electrode layer by a deposition process, the insulation layer is formed and stacked on a partial surface of the piezoelectric layer and a partial surface of the lower electrode layer by a deposition process, and the upper electrode layer is formed and stacked on the insulation layer and a remaining surface of the piezoelectric layer without the insulation layer disposed thereon by a deposition process, so as to electrically connect with the piezoelectric layer;

wherein when the piezoelectric component is driven, the gas introduced from the at least one inlet aperture of the substrate is converged to the convergence chamber through the plurality of convergence channels, and flows through the through hole of the vibration layer, whereby a resonance effect is generated by the piezoelectric component and the actuating portion of the vibration layer to transport the gas and output.

20. The wearable display device according to claim 1, wherein the heat pipe comprises a first contact surface and a second contact surface, the microprocessor is located at the first contact surface, and the first actuator and the at least one cooling chip are located at the second contact surface.

21. The wearable display device according to claim 1, wherein the heat pipe comprises a first contact surface and a second contact surface, the microprocessor and the at least one cooling chip are located at the first contact surface, and the first actuator is located at the second contact surface.

* * * * *